(12) United States Patent
Lee et al.

(10) Patent No.: US 9,688,961 B2
(45) Date of Patent: Jun. 27, 2017

(54) PROCESS OF PREPARING HUMAN MULTIPOTENT STEM CELLS CO-EXPRESSING CD34 AND CD73

(75) Inventors: Dong-Ryul Lee, Seoul (KR); Won-Yun Choi, Seoul (KR); Tae-Ki Yoon, Seoul (KR)

(73) Assignee: SUNGKWANG MEDICAL FOUNDATION, Seoul (KR)

( * ) Notice: Subject to any disclaimer, the term of this patent is extended or adjusted under 35 U.S.C. 154(b) by 384 days.

(21) Appl. No.: 14/126,220

(22) PCT Filed: Jun. 8, 2012

(86) PCT No.: PCT/KR2012/004546
§ 371 (c)(1),
(2), (4) Date: Dec. 13, 2013

(87) PCT Pub. No.: WO2012/173358
PCT Pub. Date: Dec. 20, 2012

(65) Prior Publication Data
US 2014/0120070 A1    May 1, 2014

(30) Foreign Application Priority Data
Jun. 15, 2011 (KR) .................. 10-2011-0057767

(51) Int. Cl.
C12N 5/00      (2006.01)
C12N 5/071     (2010.01)
A61K 35/48     (2015.01)
C12N 5/0775    (2010.01)

(52) U.S. Cl.
CPC .......... *C12N 5/0683* (2013.01); *A61K 35/48* (2013.01); *C12N 5/0668* (2013.01)

(58) Field of Classification Search
USPC .................................................. 435/325, 455
See application file for complete search history.

(56) References Cited

U.S. PATENT DOCUMENTS

| | | | | |
|---|---|---|---|---|
| 7,666,673 B2 * | 2/2010 | Shinohara | ............... | C12N 5/061 435/325 |
| 2004/0258670 A1 * | 12/2004 | Laughlin | ................ | A61K 35/28 424/93.21 |
| 2008/0044395 A1 | 2/2008 | Kim et al. | | |
| 2011/0008764 A1 | 1/2011 | Silva et al. | | |

FOREIGN PATENT DOCUMENTS

| KR | 10-2007-0030774 A | 3/2007 |
|---|---|---|
| WO | WO 2010/141606 | * 12/2010 |

OTHER PUBLICATIONS

Cronright et al. (Cancer Research, vol. 65, No. 6, p. 2207-2215, 2005).*
Martin-Satue et al. (Histochemistry Cell Biology, vol. 133, p. 659-668, 2010).*
Kim et al. (Stem Cells, vol. 26, No. 10, p. 2516-2522, 2008).*
Cronwright (Cancer Research, 2005, vol. 65, No. 6, p. 2207-2215).*
Martin- Satue (Histochemistry Cell Biology, 2010, vol. 133, p. 659-668).*
Kim (Stem Cells, 2008, vol. 26, No. 10, p. 2516-2522).*
Seidl (Cell Tissue Res., 1990, vol. 261, p. 539-547).*
Conrad (Nature, 2008, vol. 456, p. 344-349).*
Golestaneh (Stem Cells Dev 2009;18:1115-1126).*
Kossack (Stem Cells 2009;27:138-149).*
Mizrak (Hum Reprod 2010;25:158-167).*
Ko (Nature Jun. 2010, vol. 4654, p. E1-E3).*
Chikhovskaya (Human Reprod. 2012, vol. 27, No. 1, p. 210-221, available online Nov. 15, 2011).*
Feng (Cell Stem Cell, Apr. 3, 2009, vol. 4, p. 301-312).*
Gonzalez (Biochem. & Biophysical Res. Comm., 2009, vol. 385, p. 570-575).*
Cerilli (Arch Pathol Lab Med, 2010, vol. 134, p. 1197-1204).*
Choi (Stem Cells and Develop., 2013, vol. 22, No. 15, p. 2158-2173).*
Kim, et al., "CD34+ Testicular Stromal Cells Support Long-Term Expansion of Embryonic and Adult Stem and Progenitor Cells", Stem Cells, vol. 26, pp. 2516-2522, (2008).
Suga, et al., "Functional Implications of CD34 Expression in Human Adipose-Derived Stem/Progenitor Cells", Stem Cells and Development, vol. 18, No. 8, pp. 1201-1210, (2009).
Kanatsu-Shinohara, et al., "Long-Term Proliferation in Culture and Germline Transmission of Mouse Male Germline Stem Cells", Biology of Reproduction, vol. 69, pp. 612-616, (2003).
Ge, et al., "In search of rat stem Leydig cells: Identification, isolation, and lineage-specific development", PNAS, vol. 103, No. 8, pp. 2719-2724, (2006).
Conrad, et al., "Generation of pluripotent stem cells from adult human testis", Nature, vol. 456, pp. 344-349, (2008).
Guan, et al., "Pluripotency of spermatogonial stem cells from adult mouse testis", Nature, vol. 440, pp. 1199-1203, (2006).
Seandel, et al., "Generation of functional multipotent adult stem cells from GPR125+ germline progenitors", Nature, vol. 449, pp. 346-350, (2007).
Kanatsu-Shinohara, et al., "Generation of Pluripotent Stem Cells from Neonatal Mouse Testis", Cell, vol. 119, pp. 1001-1012, (2004).
Gonzalez, et al., "A putative mesenchymal stem cells population isolated from adult human testes", Biochemical and Biophysical Research Communications, vol. 385, pp. 570-575, (2009).
Lim, et al., "Long-term proliferation and characterization of human spermatogonial stem cells obtained from obstructive and non-obstructive azoospermia under exogenous feeder-free culture conditions", Cell Prolif., vol. 43, pp. 405-417, (2010).
Lee, et al., "Evaluation of 28 Human Embryonic Stem Cell Lines for Use as Unrelated Donors in Stem Cell Therapy: Implications of HLA and ABO Genotypes", Cell Transplantation, vol. 19, pp. 1383-1395, (2010).

(Continued)

*Primary Examiner* — Michael Wilson
(74) *Attorney, Agent, or Firm* — Vorys, Sater, Seymour & Pease LLP; Mih Suhn Koh

(57) ABSTRACT

The present invention relates to testis somatic cell-derived pluripotent stem cells, and more particularly, to pluripotent adult stem cells which exhibit a positive immune reaction to both CD34 and CD73 and which are derived from testis somatic cells. The present invention further relates to a method for producing the testis somatic cell-derived pluripotent stem cells, and to a pharmaceutical composition including same for the treatment of erectile dysfunction.

7 Claims, 40 Drawing Sheets

(56) References Cited

OTHER PUBLICATIONS

Kossack, et al., "Isolation and Characterization of Pluripotent Human Spermatogonial Stem Cell-Derived Cells", Stem Cells, vol. 27, pp. 138-149, (2009).
Golestaneh, et al., "Pluripotent Stem Cells Derived From Adult Human Testes", Stem Cells and Development, vol. 18, No. 8, pp. 1115-1126, (2009).
Mizrak, et al., "Embryonic stem cell-like cells derived from adult human testis", Human Reproduction, vol. 25, No. 1, pp. 158-167, (2010).
Tapia, et al., "Concise Review: Challenging the Pluripotency of Human Testis-Derived ESC-Like Cells", Stem Cells, vol. 29, pp. 1165-1169, (2011).
Chikhovskaya, et al., "Human testis-derived embryonic stem cell-like cells are not pluripotent, but possess potential of mesenchymal progenitors", Human Reproduction, vol. 27, No. 1, pp. 210-221, (2012).
Ko, et al., Human adult germline stem cells in question, Nature, vol. 465, pp. E1-E3; discussion E3; (2010).

* cited by examiner

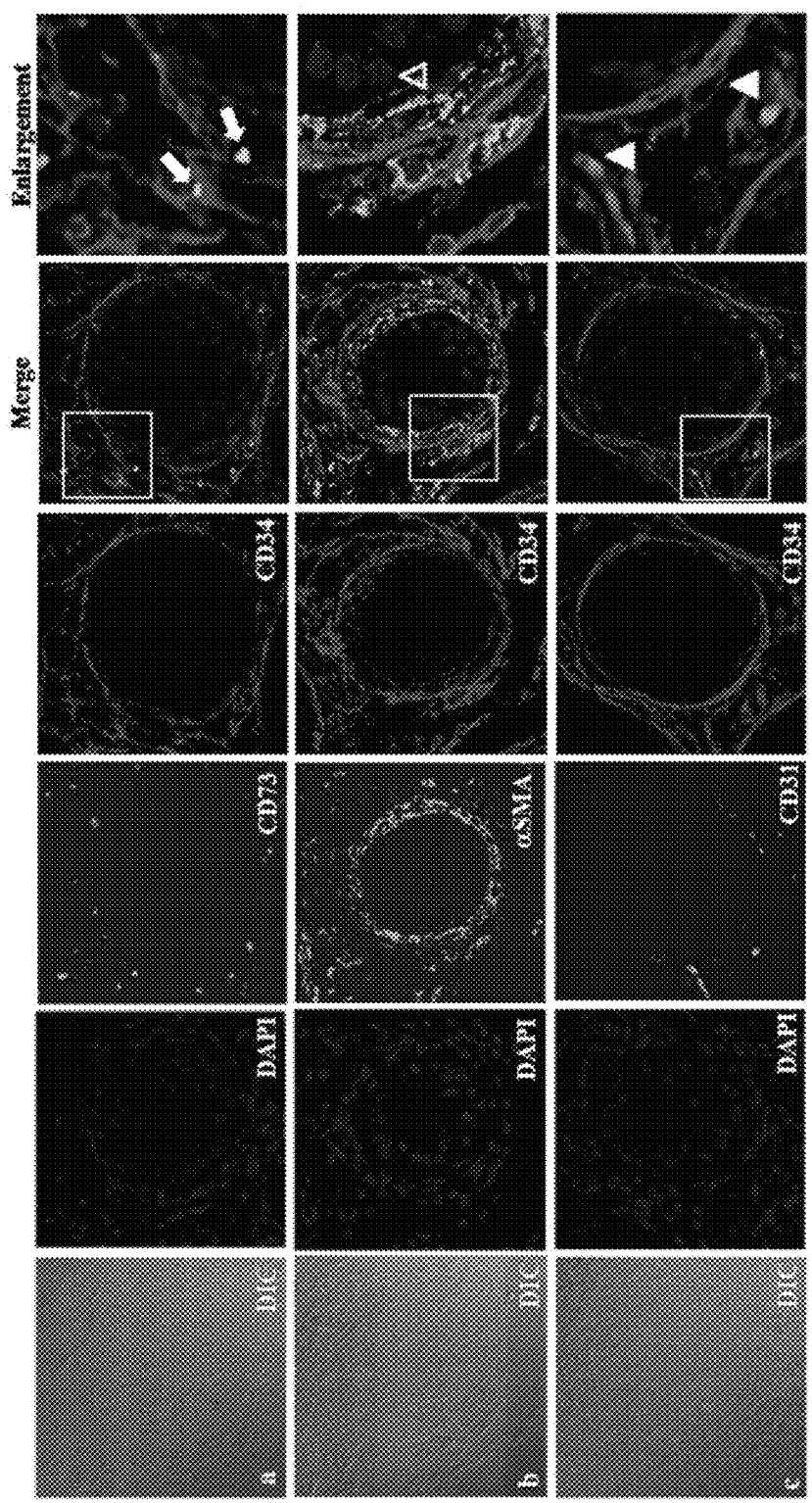

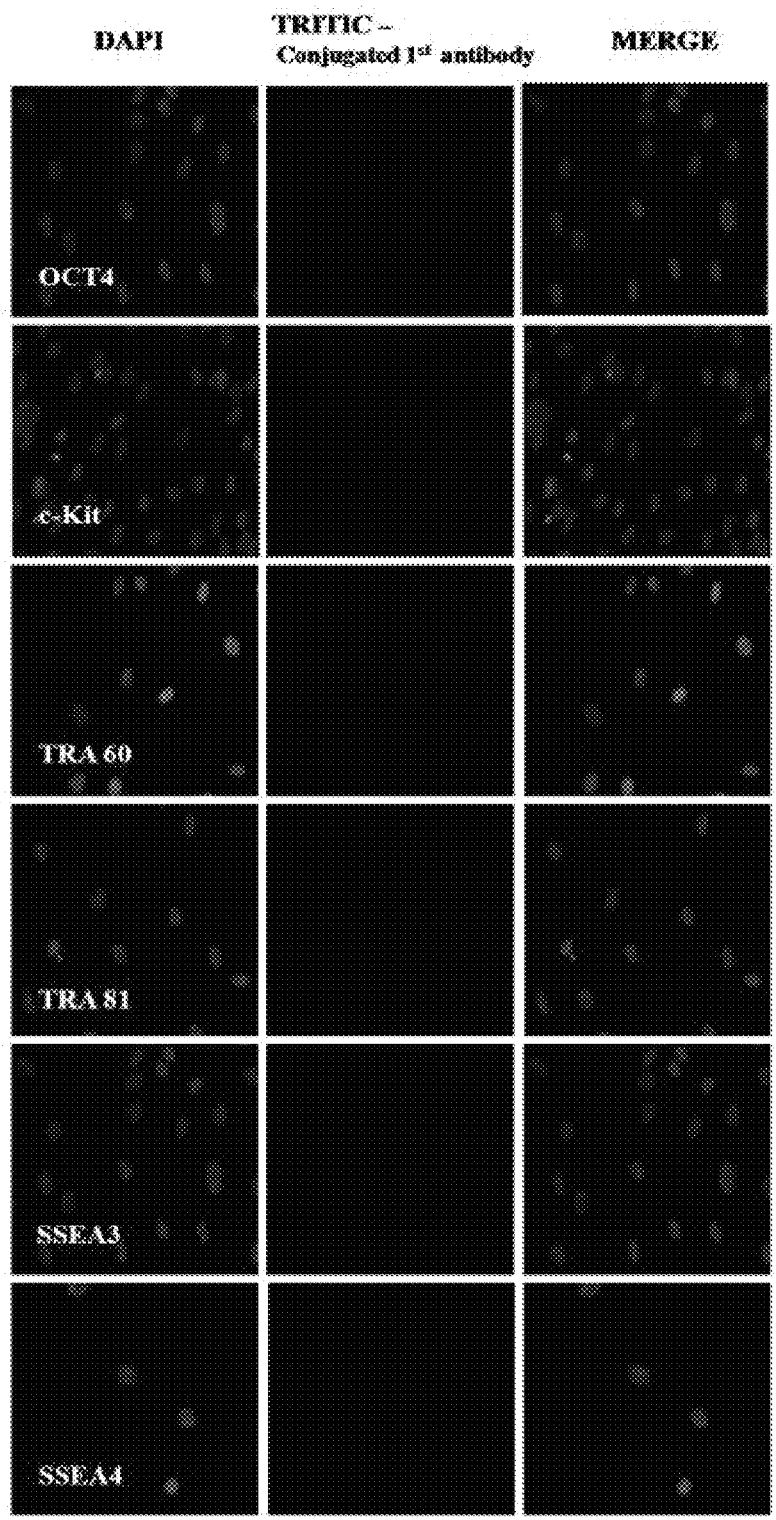

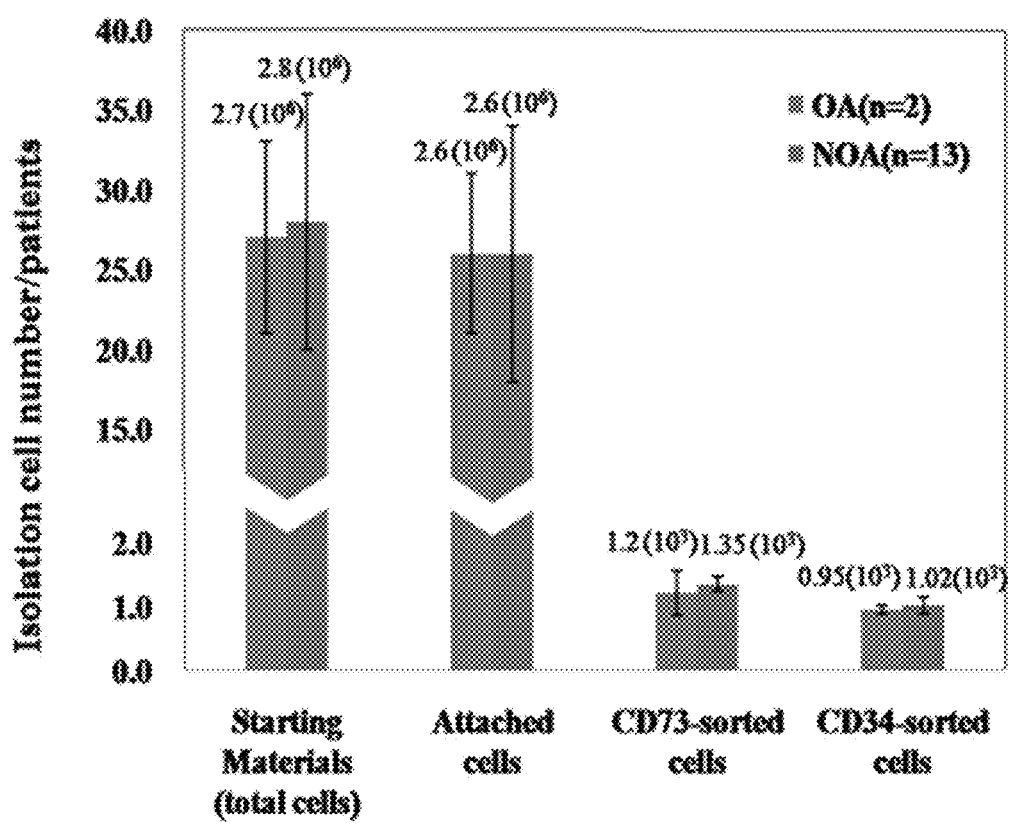

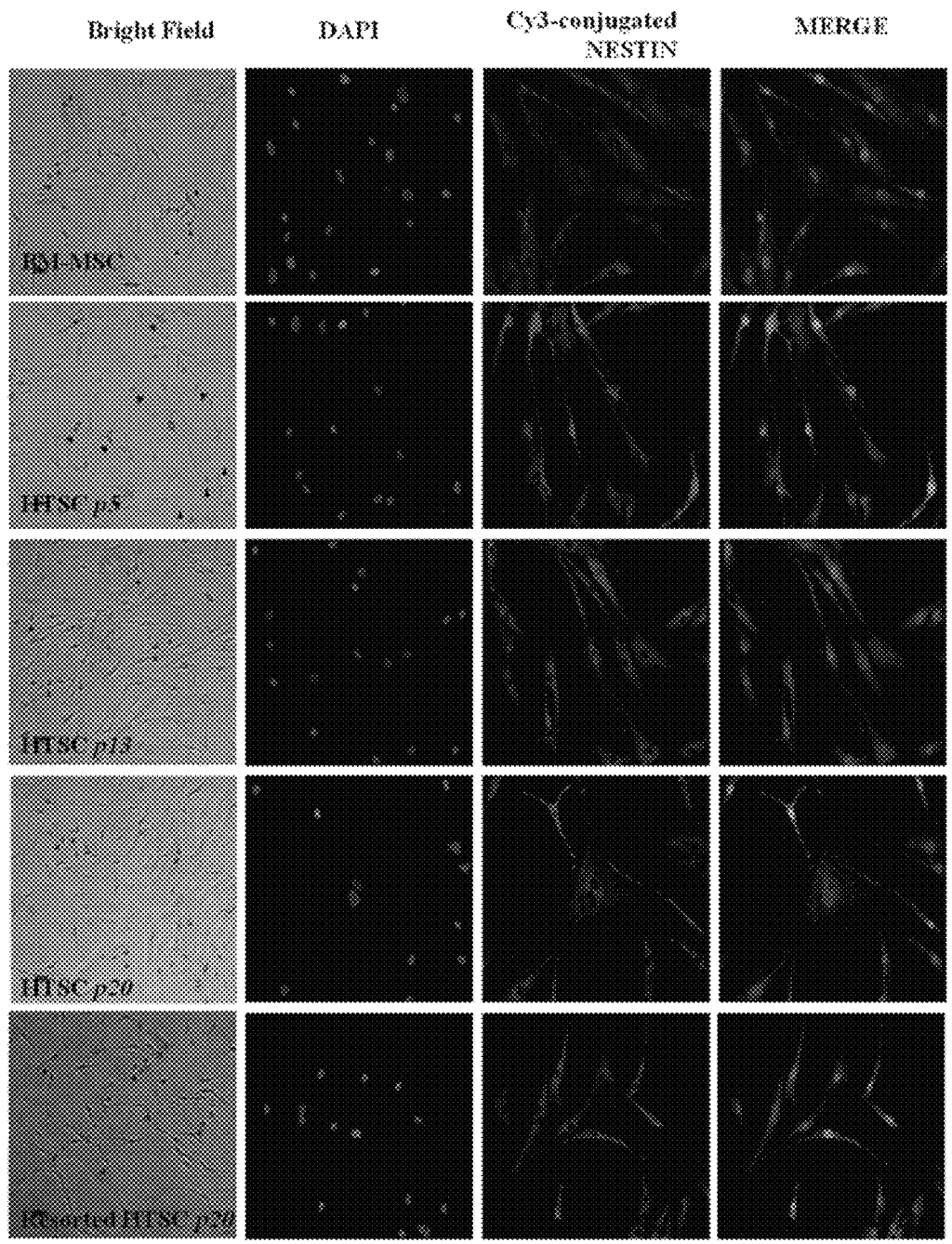

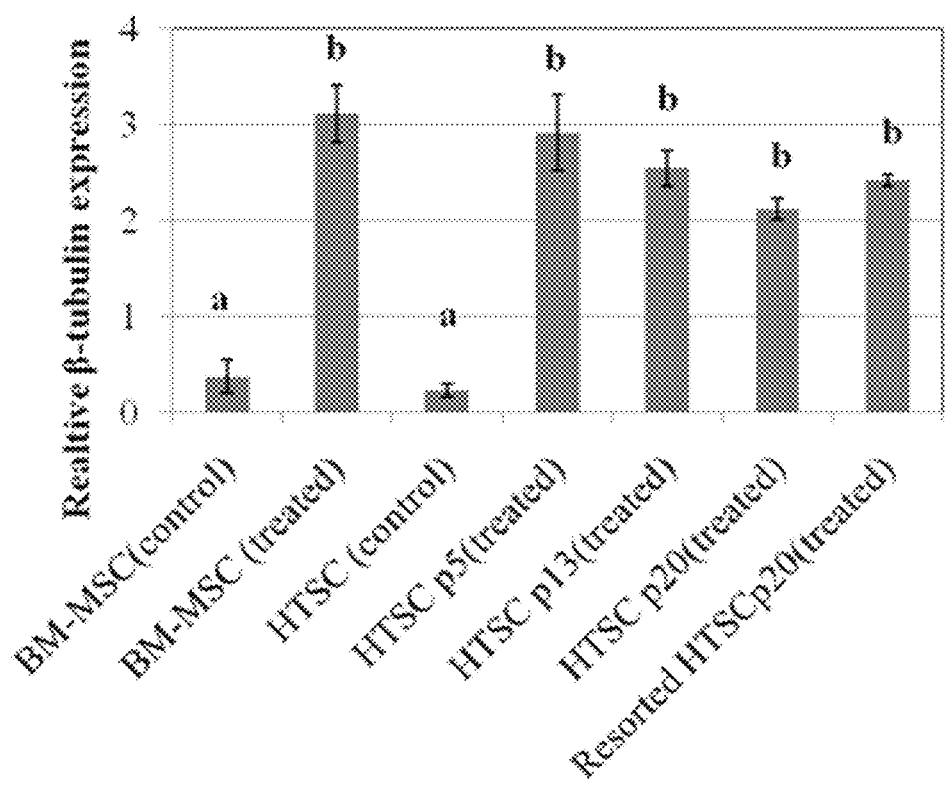

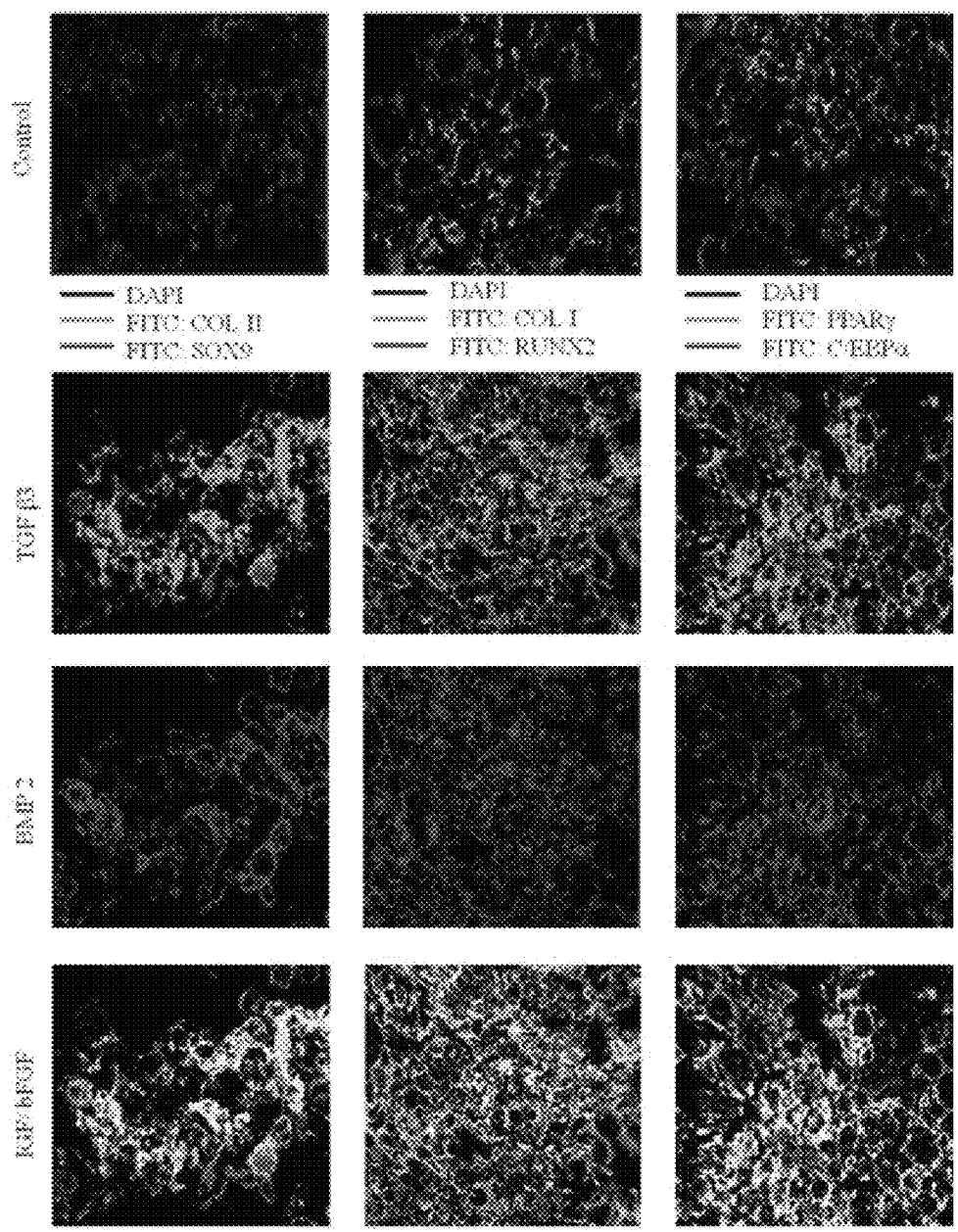

PROCESS OF PREPARING HUMAN MULTIPOTENT STEM CELLS CO-EXPRESSING CD34 AND CD73

TECHNICAL FIELD

The present invention relates to novel testicular somatic cells-derived pluripotent stem cells, more specifically to pluripotent adult stem cells derived from testicular somatic cells, which exhibit positive immune response to both CD34 and CD73. And also, the present invention relates to a process for preparing the testicular somatic cells-derived pluripotent stem cells and to a pharmaceutical composition for treating erectile dysfunction comprising the same.

BACKGROUND ART

Human adult tissue-specific stem cells have clinical utility due to their ability to repair and/or replace damaged tissue. However, identification of adult stem cells has proven to be difficult, because of a lack of proper tissue-specific stem cell markers. Limiting their clinical application further, they have a finite lifespan in culture and restricted differentiation capacity, especially compared to human embryonic stem cells (ESCs). Among adult stem cells that have been isolated thus far, bone marrow-derived mesenchymal stem cells (BM-MSCs) are the most well characterized. The BM-MSCs were identified over 10 years ago and give rise to various differentiated cell types of mesodermal origin. However, isolation of BM-MSCs is quite painful for patients and once isolated, they are difficult to maintain in culture because they reach senescence rapidly (usually by 8 passages), lose their differentiation capacity rapidly, and, on some occasions, become neoplastic after extended in vitro culture. Other source of stem cells include dental pulp, Wharton's jelly, amniotic membrane, and adipose tissue, yet all of them have limited lifespan and differentiation capabilities.

Among the specific stem cell markers, CD34 is found on early hematopoietic and vascular-associated tissues. CD34 is a 116-kD type I transmembrane glycophosphoprotein: however, little is known about its exact function. In the hematopoietic system, cells expressing CD34 on the surface can, upon cytokine or growth factor stimulation, expand and differentiate into all the lymphohematopoietic lineages. Thus, CD34 has been used as a marker to assist in the identification and isolation of lymphohematopoietic stem/progenitor cell populations; more recently, it has been employed as a marker to help identify other tissue-specific stem cells, including muscle satellite cells and epidermal precursors. Recently, it has found that CD34-positive stromal cells are distributed in various organs including breast, fallopian tubes, thyroid gland, colon, pancreas, uterine cervix, and testis (Kim J, Seandel M, Falciatori I, et al. CD34+ testicular stromal cells support long-term expansion of embryonic and adult stem and progenitor cells. Stem Cells. 2008; 26:2516-2522). In adipose-derived stromal cell (ASC) populations, CD34-positive cells are resident pericytes that play a role in vascular stabilization by mutual structural and functional interactions with endothelial cells. In another study, CD34-positive cells showed higher proliferative and colony-forming capacity than CD34-negative cells, but lower differentiating capability. Thus, the authors suggested that CD34 expression was inversely correlated to the physiological process of differentiation from an immature status into specific lineages (Suga H, Matsumoto D, Eto H, et al. Functional implications of CD34 expression in human adipose-derived stem/progenitor cells. Stem Cells Dev. 2009; 18:1201-1210). However, CD73 is a glycosyl phosphatidylinositol (GPI)-linked, membrane-bound glycoprotein that hydrolyzes extracellular nucleoside monophosphates into bioactive nucleoside intermediates. This antigen is found in most cell types including mesenchymal stem cells, subsets of B-cells and T-cells and endothelial cells. Thus, this molecule has been used as a maker to identify MSCs originating from several different tissues. Interestingly, almost none of the MSCs isolated so far show both CD73 and CD34 expression.

Meanwhile, mammalian testis consists of germ cells and various types of somatic cells. The lack of specific markers has made it difficult to identify and localize potential stem cells in tissues. Several researchers have isolated and propagated unipotent stem cells such as spermatogonial stem cells (SSCs) and Leydig stem cells (Kanatsu-Shinohara M, Ogonuki N, Inoue K, et al. Long-term proliferation in culture and germline transmission of mouse male germline stem cells. Biol Reprod. 2003; 69:612-616; and Ge R S, Dong Q, Sottas C M, et al. In search of rat stem Leydig cells: identification, isolation, and lineage-specific development. Proc Natl Acad Sci USA. 2006; 103:2719-2724). In addition, primordial germ cell-derived embryonic stem cell-like cells have been generated using testis biopsies from both human and mouse (Conrad S, Renninger M, Hennenlotter J, et al. Generation of pluripotent stem cells from adult human testis. Nature. 2008; 456:344-349; Guan K, Nayernia K, Maier L S, et al. Pluripotency of spermatogonial stem cells from adult mouse testis. Nature. 2006; 440:1199-1203; Seandel M, James D, Shmelkov S V, et al. Generation of functional multipotent adult stem cells from GPR125+ germline progenitors. Nature. 2007; 449:346-350; Kanatsu-Shinohara M, Inoue K, Lee J, et al. Generation of pluripotent stem cells from neonatal mouse testis. Cell. 2004; 119:1001-1012). These cells differentiated into cells of all 3 germ layers and formed tumors when they were injected into NOD-SCID mice (Conrad S, Renninger M, Hennenlotter J, et al. Generation of pluripotent stem cells from adult human testis. Nature. 2008; 456:344-349).

However, studies on testis somatic stem cells have been rare. Only recently was a MSC-like population isolated in adult human testes and partially characterized by differentiating it into mesodermal-lineage cells (Gonzalez R, Griparic L, Vargas V, et al. A putative mesenchymal stem cells population isolated from adult human testes. Biochem Biophys Res Commun. 2009; 385:570-575). These cells were positive for CD90 and negative for CD34, suggesting they were testis-derived MSCs with limited lifespans in vitro. In the mouse, CD34-positive stromal cells efficiently support the proliferation of adult spermatogonial progenitor cells (Seandel M, James D, Shmelkov S V, et al. Generation of functional multipotent adult stem cells from GPR125+ germline progenitors. Nature. 2007; 449:346-350). However, no study has been carried out to determine if CD34/CD73-double-positive testis stromal cells are another somatic stem cell source and, if so, what their differentiation and proliferation capabilities are.

DISCLOSURE

Technical Problem

The present inventors has found that CD34/CD73-double-positive cells exhibited remarkably excellent proliferative capacity and remarkably high differentiation potential into cells of adipogenic, osteogenic, neuronal, and pancreatic lineages, in comparison with CD34-negative ones. The cells did not form teratomas in NOD-SCID mice and retained high genetic stability as indicated by their normal karyotype after 30 passages. They also promoted a functional recovery of penile erection in a bilateral cavernous nerve crush injury model in rats. Additionally, the percent of cells expressing CD34 decreased as the passage number of the cells increased in vitro and as the cells became terminally differentiated.

Therefore, it is an object of the present invention to provide testicular somatic cells-derived CD34/CD73-double-positive pluripotent adult stem cells.

It is another object of the present invention to provide a process for preparing the testicular somatic cells-derived CD34/CD73-double-positive pluripotent adult stem cells.

It is still another object of the present invention to provide a pharmaceutical composition for treating erectile dysfunction, comprising the testicular somatic cells-derived CD34/CD73-double-positive pluripotent adult stem cells an active ingredient.

Technical Solution

In accordance with an aspect of the present invention, there is provided pluripotent adult stem cells derived from testicular somatic cells, which exhibit positive immune response to both CD34 and CD73.

In accordance with another aspect of the present invention, there is provided a process for preparing pluripotent adult stem cells which exhibit positive immune response to both CD34 and CD73, the process of which comprising: (a) isolating outer surrounding cells of seminiferous tubules from a human testis tissue that has been externally discharged from a human body, and then subculturing the isolated cells; and (b) carrying out cell-sorting of the cells obtained in the step (a) with an anti-CD34 antibody and an anti-CD73 antibody to isolate both CD34-positive and CD73-positive cells, and then subculturing the isolated cells.

In accordance with still another aspect of the present invention, there is provided a pharmaceutical composition for treating erectile dysfunction, comprising pluripotent adult stem cells derived from testicular somatic cells, which exhibit positive immune response to both CD34 and CD73, as an active ingredient.

Advantageous Effects

CD34/CD73-double-positive testis stromal cells, i.e., testicular somatic cells-derived pluripotent adult stem cells, are newly isolated by the present invention. The pluripotent adult stem cells exhibit remarkably excellent proliferative capacity (about average of 67.3±2.1 population doublings) and remarkably high differentiation potential into three germ layer lineage cells including adipogenic cells, osteogenic cells, neurogenic cells, and pancreatic cells (e.g., insulin-secreting cells). The pluripotent adult stem cells do not form teratomas and retained high genetic stability as indicated by their normal karyotype even after 30 passages. Especially, the pluripotent adult stem cells promote a functional recovery of penile erection in a bilateral cavernous nerve crush injury model in rats. Therefore, the pluripotent adult stem cells can be usefully applied to a pharmaceutical composition for treating erectile dysfunction.

DESCRIPTION OF DRAWINGS

FIG. 2 shows specific marker expression by bone marrow-derived mesenchymal stem cells (BM-MSCs), testis-derived stem cells (TSCs) and highly proliferative testis-derived stem cells (HTSCs). FIG. 2c is the result of immunocytochemistry analysis which shows lack of expression of pluripotent stem cell markers (OCT4, c-Kit, Tra-1-60, Tra-1-81, SSEA3 and SSEA4) in HTSCs; FITC staining is green; Cy3 and TRITC staining is red.

FIG. 3 shows morphological and proliferative characteristics of various types of testis-derived stem cells (TSCs).

FIG. 4 shows the flow cytometry of sorted populations before and after further culture.

FIG. 5 shows in vitro differentiation potential into mesodermal-lineage (chondrogenic, adipogenic, and osteogenic) cells of bone marrow-derived mesenchymal stem cells (BM-MSCs), testis-derived stem cells (TSCs), and highly proliferative testis-derived stem cells (HTSCs).

FIG. 6 shows in vitro differentiation potential of bone marrow-derived mesenchymal stem cells (BM-MSCs) and highly proliferative testis-derived stem cells (HTSCs) into insulin-secreting cells.

FIG. 9b shows separated cell numbers in each step per 100 mg of testis tissue. Starting materials were counted at Day 0, attached cells were at Day 3, CD73-sorted cells were at p2 and CD34-sorted cells were at p3.

FIG. 11 shows characteristics of highly proliferative testis-derived stem cells (HTSCs).

FIG. 15 shows in vitro differentiation potential of bone marrow-derived mesenchymal stem cells (BM-MSCs) and highly proliferative testis-derived stem cells (HTSCs) into neuronal-lineage cells. FIG. 15a shows that Nestin was expressed in differentiated neuronal cells from BM-MSCs and HTSCs (×200). FIG. 15c shows gene expression of GFAP and β-Tubulin 3 in cells subjected to neurogenic differentiation in induced HTSCs compared to BM-MSCs.

FIG. 16 shows in vivo differentiation potential into mesodermal-lineage (adipogenic, osteogenic and chondrogenic) cells of highly proliferative testis-derived stem cells (HTSCs). FIG. 16c and FIG. 16d show the results of immunocytochemistry analyses using specific staining and specific markers.

BEST MODE

Figure 1B:
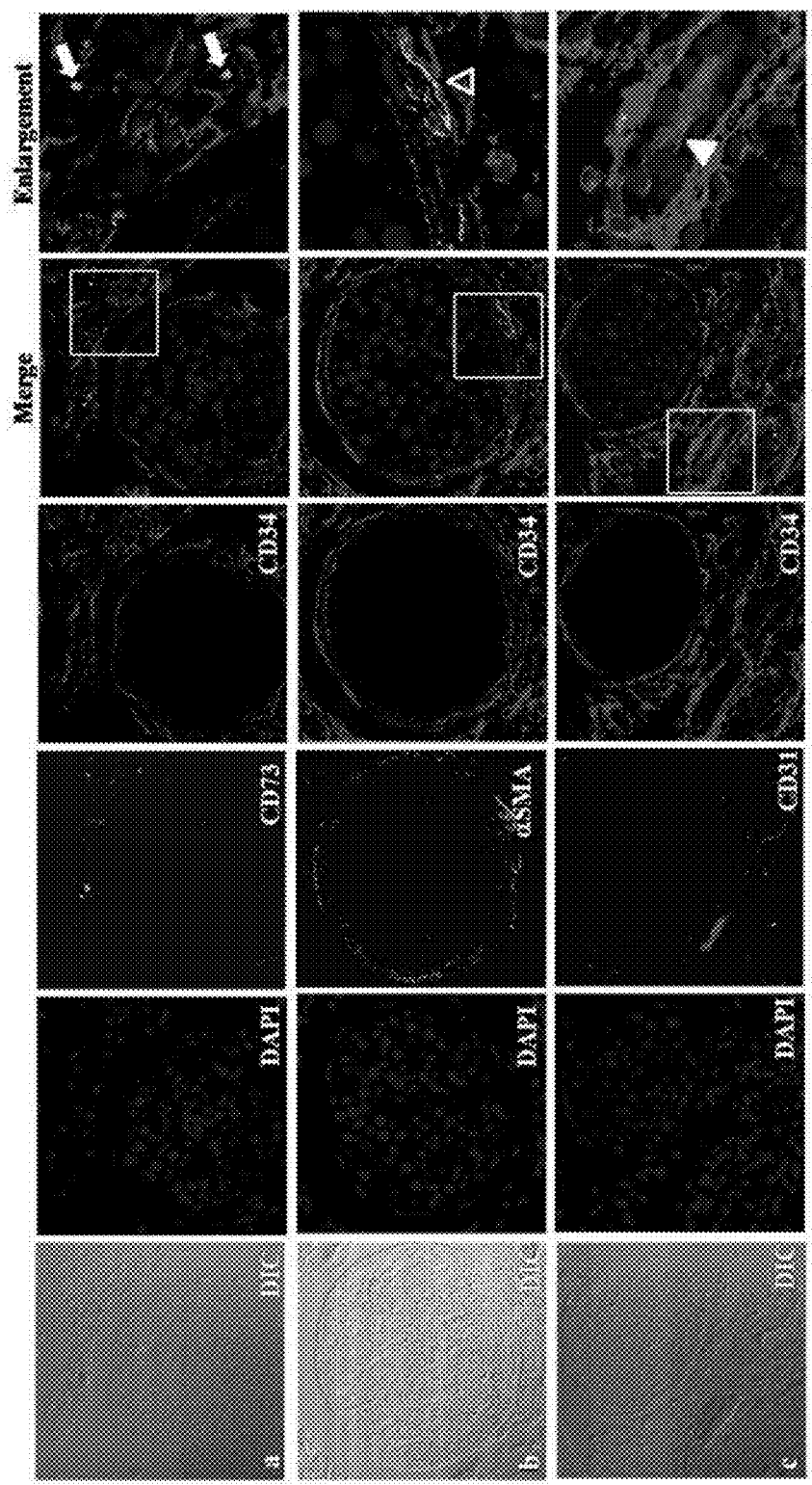
FIG. 1 shows co-localization of CD34 and CD73, αSMA, and CD31 in human testis tissue of non-obstructive azoospermia (NOA, FIG. 1a) and obstructive azoospermia (OA, FIG. 1b). DAPI nuclear staining is in blue; FITC staining is green; Cy3 staining is red. White arrows are CD34, CD73-double positive signals. Open arrowheads are signals for αSMA. White arrowheads are signals for CD31.

The present invention provides pluripotent adult stem cells derived from testicular somatic cells, which exhibit positive immune response to both CD34 and CD73.

The pluripotent adult stem cells according to the present invention exhibit excellent proliferative capacity (about average of 67.3±2.1 population doublings) and remarkably high differentiation potential into three germ layer lineage cells including adipogenic cells, osteogenic cells, neurogenic cells, and pancreatic cells (e.g., insulin-secreting cells). The pluripotent adult stem cells do not form teratomas and retained high genetic stability as indicated by their normal karyotype even after 30 passages. In the pluripotent adult stem cells, the testicular somatic cells may be outer surrounding cells of seminiferous tubules, preferably interstitial cells.

The present invention also provides a process for preparing said pluripotent adult stem cells. That is, the present invention provides a process for preparing pluripotent adult stem cells which exhibit positive immune response to both CD34 and CD73, the process of which comprising: (a) isolating outer surrounding cells of seminiferous tubules from a human testis tissue that has been externally discharged from a human body, and then subculturing the isolated cells; and (b) carrying out cell-sorting of the cells obtained in the step (a) with an anti-CD34 antibody and an anti-CD73 antibody to isolate both CD34-positive and CD73-positive cells, and then subculturing the isolated cells.

As used herein, the human testis tissue that has been externally discharged from a human body refers to the male testis tissues which are conventionally collected in fertility clinics for clinical purposes. In case of male infertility patients, for example azoospermic patients, testis tissues are collected for the treatment of testicular sperm extraction and intracytoplasmic sperm injection (TESE-ICSI). After the testis tissues are clinically used, the remaining tissues are discarded. The male testis tissues externally discharged from a human body, such as the testis tissues discarded in fertility clinics etc., may be used in the process of the present invention. The testis tissues may be tissues obtained from obstructive or non-obstructive azoospermic patients.

Outer surrounding cells of seminiferous tubules, preferably interstitial cells of seminiferous tubules, may be isolated through enzymatic treatment of the testis tissues externally discharged from a human body, preferably testis tissues washed with RBC lysis buffer. For example, the isolation may be performed by enzymatically treating the human testis tissue that has been externally discharged from a human body with collagenase, dispase, or a mixture thereof. The enzymatic treatment may be performed by agitating at about 37° C. for about 30 minutes.

The obtained outer surrounding cells of seminiferous tubules (e.g., interstitial cells) may be subcultured in a conventional cell culture medium, for example in a medium comprising feeder cells and serum, up to passage 2 to passage 4, preferably up to passage 3. In an embodiment, the feeder cells may be gelatin. And also, a mixed medium of DMEM-F12 (Gibco) and Stempro 34 (Invitrogen Corporation, Camarillo, Calif.) supplemented with fetal bovine serum and penicillin/streptomycin may be used as a serum-containing medium. When cells reach e.g., 80% confluency in a subculture, the cells may be detached into single cells using e.g., Trysin-EDTA, followed by subsequent subculturing.

The process of the present invention comprises carrying out cell-sorting of the cells obtained in the step (a) with an anti-CD34 antibody and an anti-CD73 antibody to isolate both CD34-positive and CD73-positive cells, and then subculturing the isolated cells [i.e., step (b)].

The cell-sorting may be performed according to conventional methods in the field of biotechnology, preferably according to magnetic activating-cell sorting (MACS). The MACS, which is a method for isolating cells responsive to a specific marker, may be performed by using e.g., Dynabeads Flowcomp (Invitrogen) etc. The MACS may be carried out with an anti-CD34 antibody and an anti-CD73 antibody, according to methods disclosed in the present inventors' previous literature [Lim, J. J., et al. Long-term proliferation and characterization of human spermatogonial stem cells obtained from obstructive and non-obstructive azoospermia under exogenous feeder-free culture conditions. *Cell Prolif* 43, 405-417 (2010)]. The literature is incorporated herein by reference in its entirety.

The subculturing of the step (b) may be performed up to passage 7 to passage 9 in a medium comprising feeder cells and serum. In an embodiment, the feeder cells may be gelatin. The serum-containing medium may be a mixed medium of DMEM-F12 (Gibco) and Stempro 34 (Invitrogen Corporation, Camarillo, Calif.) supplemented with fetal bovine serum and penicillin/streptomycin, but not limited thereto. When cells reach e.g., 80% confluency in a subculture, the cells may be detached into single cells using e.g., Trysin-EDTA, followed by subsequent subculturing.

When the cells sorted by MACS with an anti-CD34 antibody and an anti-CD73 antibody as in the step (b) are subcultured for long duration, the number of CD34-positive stem cells may significantly decrease after passage 7 to passage 9 (about passage 8). The present inventors have found that, when the cells subcultured up to passage 7 to passage 9 (about passage 8) are subject to additional cell-sorting (for example, additional cell-sorting through MACS), the CD34-positive stem cells can be maintained even in the subcultures for longer duration.

Therefore, in an embodiment, the process of the present invention may further comprise carrying out cell-sorting, preferably cell-sorting through MACS [i.e., second MACS], of the cells performed up to passage 7 to passage 9 with an anti-CD34 antibody, followed by additional subculturing. The additional subculturing may be performed up to passage 7 to passage 12, in addition to the subculturing of the step (b). For example, if the initial subcultures in the step (b) are preformed up to passage 8, total subcultures may be performed up to passage 15 to passage 20.

In another embodiment, the additional subculturing may be performed by subculturing up to passage 12 in addition to the subculturing of the step (b) [for example, if the initial subcultures in the step (b) are preformed up to passage 8, total subcultures are performed up to passage 20]; carrying out cell-sorting, preferably cell-sorting through MACS [i.e., third MACS], of the resulting cells with an anti-CD34 antibody; and then performing subsequent subculturing.

The present invention also provides a pharmaceutical composition for treating erectile dysfunction, comprising pluripotent adult stem cells derived from testicular somatic cells, which exhibit positive immune response to both CD34 and CD73, as an active ingredient.

We have found that bilateral cavernous nerve crush injuries (BCNCI) are recovered by topical administration of the pluripotent adult stem cells obtained according to the present invention to periprostatic areas of BCNCI rats. Therefore, the pluripotent adult stem cells can be usefully applied for treating erectile dysfunction. Especially, since the CD34 and CD73 double-positive pluripotent adult stem cells obtained according to the present invention do not form teratomas, the cells may be safely administered to patients. Generally, prostate cancer is diagnosed through transrectal biopsy of the prostate (e.g., radical prostatectomy). In this case, autologous testis-derived stem cells can be prepared from the resulting testicular biopsies, according to the process of the present invention; and therefore, said pluripotent adult stem cells can be administered without safety problems such as immune incompatibility. Accordingly, the pharmaceutical compositions of the present invention may be suitably applied in order to treat the erectile dysfunction caused by radical prostatectomy.

The pharmaceutical composition of the present invention may include a pharmaceutically acceptable carrier, along with said CD34-positive and CD73-positive pluripotent adult stem cells derived from testicular somatic cells; and formulated into parenteral dosage forms such as solution, suspension, emulsion, lyophilized formulation, according to conventional methods. The pharmaceutically acceptable carrier includes aqueous diluent or solvent, such as phosphate buffered saline, purified water, sterilized water. If necessary, conventional preservatives may be included.

In the pharmaceutical composition of the present invention, a dose of the CD34-positive and CD73-positive pluripotent adult stem cells derived from testicular somatic cells may vary depending on erectile dysfunction patients' state and body weight, seriousness of disease, dosage forms, administration routes, and the period of administration. For example, the CD34-positive and CD73-positive pluripotent adult stem cells derived from testicular somatic cells may be administered in a dose of $10^5$ to $10^8$ cells/ml per administration, but not limited thereto.

The present invention will be described in further detail with reference to the following examples. However, these examples are for illustrative purposes only and are not intended to limit the scope of the present invention.

1. Materials and Methods (1) Isolation and Culture of Human Highly Proliferative Testis-Derived Stem Cells (HTSCs)

Twenty-five samples of testis tissue, remaining after clinical requirements, were obtained from patients undergoing testicular sperm extraction and intracytoplasmic sperm injection (TESE-ICSI) treatment, under each patient's informed consent. Ten samples were discarded during passage 1-2 because the cells were positive for *mycoplasma* contamination (MycoAlert®, *mycoplasma* detection kit, Lonza, Rockland, Me.). Finally, the testicular tissue samples obtained from obstructive (OA, n=2) or non-obstructive azoospermic (NOA, n=13) patients were used in the study. This study was approved by the Institutional Review Board of the CHA Gangnam Medical Center (Seoul, Republic of Korea).

Figure 8:
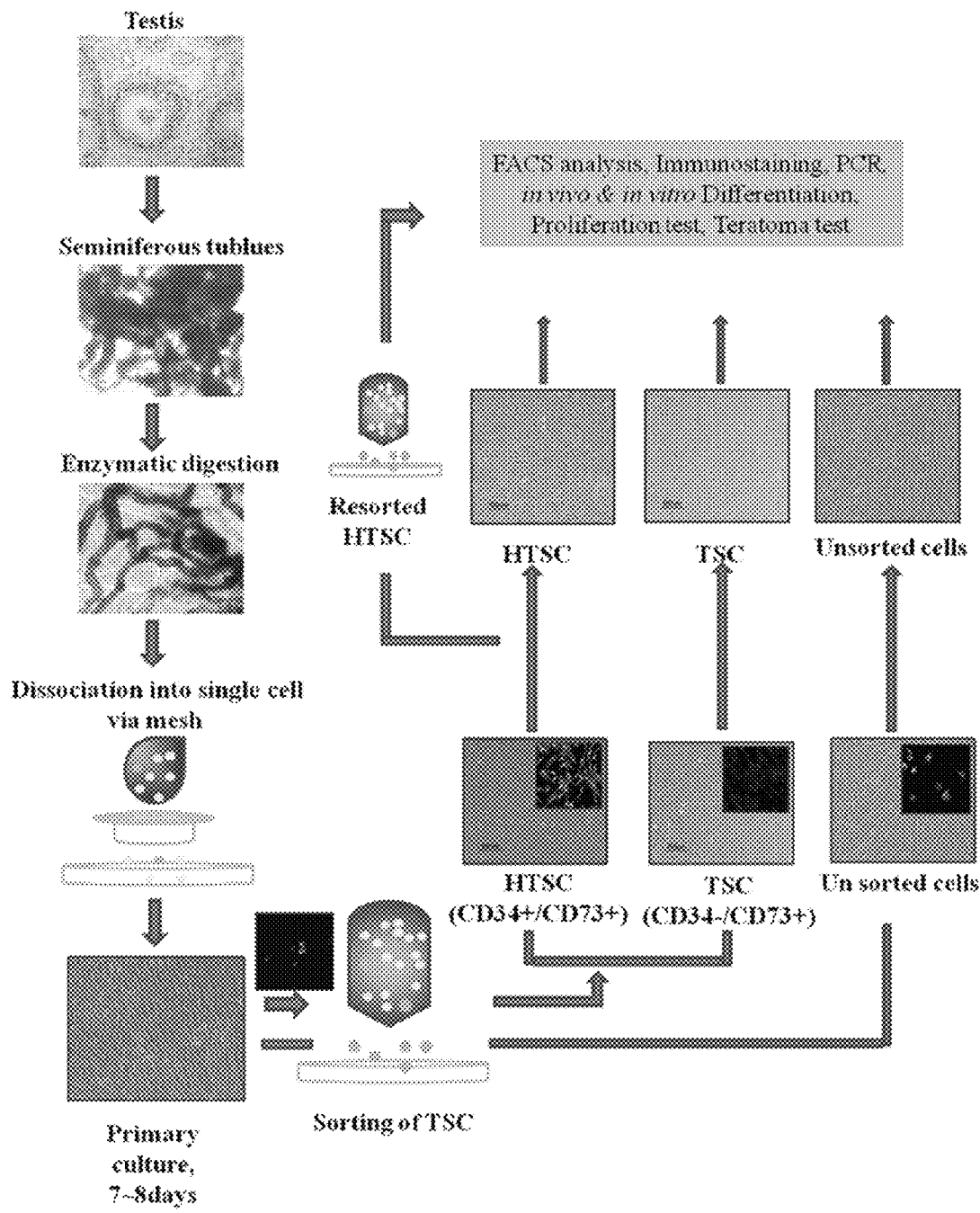
FIG. 8 shows an example of the procedure for isolating CD34-positive and CD73-positive testis-derived mesenchymal stem cells.

The overall study design is summarized in the flow chart of FIG. 8. Testis tissues were washed with RBC lysis buffer (Roche Diagnostics, Basel, Switzerland) and interstitial cells of intact seminiferous tubules were dissociated enzymatically with agitation at 37° C. for 30 minutes in the enzyme solution [Hanks' balanced salt solution (HBSS, Gibco, Grand Island, N.Y.) containing 0.5 mg/ml collagenase (type IV; Gibco) and 0.25 mg/ml dispase II (neutral protease, grade III, Roche)]. To isolate the interstitial cells, only outer surrounding cells of seminiferous tubule were dissociated by enzyme digestion plus mechanical separation, avoiding dissociation of tubule as much as possible. The suspension of interstitial cells was collected, washed, and filtered through a 40 μm mesh (BD, Franklin Lakes, N.J.). Then, they were plated ($5.0 \times 10^5$/ml) in culture flasks coated with 0.1% gelatin (Gibco) and cultured in basic culture medium [50:50 mixture of DMEM-F12:StemPro-34 (Invitrogen Corporation, Camarillo, Calif.) supplemented with 10% fetal bovine serum (FBS, Gibco) and penicillin/streptomycin solution (1×, Gibco)]. After 7-8 days, cells at 80% confluency were detached using 0.25% Trysin-EDTA (Gibco) and passaged. After 2-3 passages, primary cultured cells were detached and then sorted with a Dynabeads Flowcomp (Invitrogen) to obtain CD73 (Santa Cruz Biotechnology, CA)/CD34 (Santa Cruz Biotechnology)-double-positive cells. In brief, the detached cells were incubated with CD73 antibody and with biotin-conjugated goat anti-mouse IgM and then mixed with the streptavidin-bound magnetic Dynabead. After sorting, cells were incubated in releasing buffer and transferred to the Dynal MPC-1 magnet. The released CD73-positive cells were collected and additionally cultured for 4-7 days, and then were detached and subjected to a second isolation with a biotinylated CD34 antibody using the procedures described above. Sorted CD34-negative/CD73-positive cells are referred to as TSCs and were re-plated ($5.0 \times 10^5$/ml) and cultured in culture flasks coated with 0.1% gelatin (Gibco) in the basic culture medium. And also, sorted CD34-positive/CD73-positive cells are referred to HTSCs and were re-plated (1,000 cells/25 cm$^2$) and cultured in a basic culture medium for 10 to 14 days. Medium was changed every other day. The cumulative population doubling with each subculture was calculated with the formula $2^X = N_H/N_I$, where $N_I$ is the seeded cell number, $N_H$ is the cell harvest number at confluence (>80%), and X is population doubling. The calculated population doubling was then added to the previous population doubling level to yield the cumulative population doubling level.

(2) Flow Cytometric Analysis

After p2, HTSCs at 80% confluency were passaged every 3-4 days. At p5, some HTSCs were resuspended and then incubated with antibodies for 20 minutes at 4° C. in the dark to detect CD34, CD73, HLA, ABC, CD166, CD44, CD29, CD105, CD90, CD31, CD45, HLA DR, TRA-1-60, SSEA3, SSEA4, TRA-1-81, CD14 (BD), CD133 (eBioscience Inc, San Diego, Calif.), c-Kit (Santa Cruz Biotechnology) and Stro-1 (Biolegend, San Diego, Calif.). Cells were washed, suspended in 500 μl PBS, and immediately analyzed in a flow cytometer (FACS Vantage SE System, BD). To identify dead cells, we incubated HTSCs with propidium iodide (Sigma-Aldrich, St. Louis, Mo.). The percentage of cells that were positive for each specific antibody was calculated by comparison with the appropriate isotype control.

(3) Immunocytochemistry

HTSCs were fixed in 4% paraformaldehyde (PFA) and stored at 4° C. After permeabilization in 0.1% Triton X-100 (Sigma) and blocking in blocking solution (Dako Cytomation Inc., Carpinteria, Calif.), primary antibody diluted in blocking buffer was applied overnight at 4° C. Cells were incubated with secondary antibody in blocking buffer for 1 hour at room temperature and then counterstained with 4',6-diamidino-2-phenylindole (DAPI) (1:500, Jackson ImmunoResearch, West Grove, Pa.) and mounted (Dako Cytomation Inc.). The primary antibodies used were CD34 (1:100, Santa Cruz Biotechnology), CD73 (1:100, Santa Cruz Biotechnology), OCT4, c-Kit, TRA-1-60, TRA-1-81, SSEA3, SSEA4 (1:100, Chemicon, Thmecula, Calif.), GFRα1, Thy-1, 3β-HSD, Desmine, αSMC and nestin (1:100, Millipore, Billerica, Mass.). Secondary antibodies conjugated to FITC (1:200, Jackson ImmunoResearch), Cy3 (1:200, Jackson ImmunoResearch) and TRITC (1:200, Jackson ImmunoResearch) were used.

For localization of CD34 and CD73 in human testis, cryosections were fixed for 1 hour with 10% neutral buffered formalin. After washing and blocking, primary antibody diluted in blocking buffer was applied overnight at 4° C. Tissues were incubated with secondary antibody in blocking buffer for 1 hour at room temperature and then counterstained with DAPI and mounted. The primary antibodies used were CD34 (1:100, Santa Cruz Biotechnology), CD73 (1:10, Santa Cruz Biotechnology), CD31 (1:50, Abcam, Cambridge, UK), αSMA (1:50, Abcam). Secondary antibodies conjugated to FITC (1:100) or Cy3 (1:100) were used.

(4) Karyotyping

For the cytogenetic analysis of HTSC, cells at p5, 13, 20 and 30 were incubated for 3 hours in a basic culture medium containing 0.1 µg/ml colcemid (KaryoMax Colcemid Solution; Gibco). Then, they were treated with a hypotonic solution (1% sodium citrate buffer) for 30 minutes, and fixed with methanol and acetic acid (3:1, vol/vol). Cells were spread onto glass slides and dried, and chromosomes were identified by G banding. To karyotype each cell line, more than 20 metaphase chromosomes were counted by a cytogenetic expert.

hESCs (CHA-hES4 line at p72) (Lee, J. E., et al. Evaluation of 28 human embryonic stem cell lines for use as unrelated donors in stem cell therapy: implications of HLA and ABO genotypes. Cell Transplant 19, 1383-1395 (2010)), BM-MSCs at p3 (PT-2501, Lonza, Walkersville, Md.) and adipocyte-derived hMSCs (AD-MSC) at p3 (Hwang S T, Kang S W, Lee S J, et al. The expansion of human ES and iPS cells on porous membranes and proliferating human adipose-derived feeder cells. Biomaterials. 2010; 31:8012-8021).

TABLE 1

| Gene | SEQ. ID | Primer sequence | Size (bp) | Annealing Temp. (° C.) |
|---|---|---|---|---|
| β-actin | 1 | 5'-TGA AGT GTG ACG TGG ACA TC-3' | 152 | 58 |
|  | 2 | 5'-GGA GGA GCA ATG ATC TTG AT-3' |  |  |
| Oct-4 | 3 | 5'-AGC GAA CCA GTA TCG AGA AC-3' | 140 | 58 |
|  | 4 | 5'-TTA CAG AAC CAC ACT CGG AC-3' |  |  |
| NANOG | 5 | 5'-TGA ACC TCA GCT ACA AAC AG-3' | 124 | 59 |
|  | 6 | 5'-TGG TGG TAG GAA GAG TAA AG-3' |  |  |
| SOX2 | 7 | 5'-AGC TAC AGC ATG ATG CAG GA-3' | 125 | 59 |
|  | 8 | 5'-GGT CAT GGA GTT GTA CTG CA-3' |  |  |
| VASA | 9 | 5'-AGA AAG TAG TGA TAC TCA AGG ACC AA-3' | 285 | 58 |
|  | 10 | 5'-TGA CAG AGA TTA GCT TCT TCA AAA GT-3' |  |  |
| COL I | 11 | 5'-AGA ACA TCA CCT ACC ACT GC-3' | 350 | 57 |
|  | 12 | 5'-ATG TCC AAA GGT GCA ATA AT-3' |  |  |
| CBFA 1 | 13 | 5'-CCG CAC GAC AAC CGC ACC AT-3' | 290 | 61 |
|  | 14 | 5'-CGC TCC GGC CCA CAA ATC TC-3' |  |  |
| PPAR γ | 15 | 5'-TGT CTC ATA ATG CCA TCA GG TTG-3' | 250 | 57 |
|  | 16 | 5'-GAT AAC GAT GGT GAT TTG TCT GTT-3' |  |  |
| C/EBPa | 17 | 5'-GCA AAC TCA CCG CTC CAA ATG-3' | 247 | 57 |
|  | 18 | 5'-TTA GGT TCC AAG CCA TCA GGT TTG-3' |  |  |
| COMP | 19 | 5'-AAC GCT GAA AGA TCA CGC TCA C-3' | 250 | 61 |
|  | 20 | 5'-GGT ACC AAA GAT GAA GCC C-3' |  |  |
| SOX 9 | 21 | 5'-TTC ATG AAG AG ACC GAC GA-3' | 350 | 57 |
|  | 22 | 5'-CAC ACC ATG AAG GCG TTC AT-3' |  |  |
| GFAP | 23 | 5'-CTG GAG GTT GAG AGG GAC AAT CT-3' | 317 | 57 |
|  | 24 | 5'-TAC TGC GTG CGG ATC TCT TTC-3' |  |  |
| β-tublin 3 (TUBB3) | 25 | 5'-GCC AAG TTC TGG GAA GTC AT-3' | 209 | 57 |
|  | 26 | 5'-GGC CTG AAG AGA TGT CCA AA-3' |  |  |
| NGN3 | 27 | 5'-CGT GAA CTC CTT GAA CTG AGC AG-3' | 221 | 61 |
|  | 28 | 5'-TGG CAC TCC TGG GAC AAA TTT C-3' |  |  |
| Insulin | 29 | 5'-AAC CAA CAC CTG TGC GGC TC-3' | 322 | 59 |
|  | 30 | 5'-AAG GGC TTT ATT CCA TCT CTC TCG-3' |  |  |
| GAPDH | 31 | 5'-CGC TGA GTA CGT CGT GGA GT-3' | 366 | 61 |
|  | 32 | 5'-ATG ATG TTC TGG AGA GCC CC-3' |  |  |

(5) Real Time-RT-PCR

RNA was isolated using Tri-reagent (Sigma-Aldrich) according to the manufacturer's instructions. The purity of RNA was assessed using a spectrophotometer (ND-1000, NanoDrop, Thermo Scientific, Wilmington, Del.). Reverse transcription-polymerase chain reaction (RT-PCR) was performed using a Prime script $1^{st}$ strand cDNA Synthesis Kit (TaKaRa Bio Inc, Otsu, Shiga, Japan). Subsequent PCR reactions were performed using cDNA, primer pairs of the following table 2 and RNAs from TSC at p5, HTSCs at p5, Target mRNAs were quantified relative to β-actin. Amplification products were quantified on a DNA Engine 2 fluorescence detection system (MJ research) using the DyNAmo SYBR Green qPCR kit (Finnzymes, Espoo, Finland). Reactions were performed in a reaction mixture containing 4 µl DEPC-treated water, 2 µl forward primer (5 pmol), 2 µl reverse primer (2 pmol), 10 µl premix with SYBR Green, and 2 µl cDNA template in a total volume of 20 µl. Fluorescence was measured at the end of each cycle during the 72° C. extension step. In the final step of the real-time PCR, a melting curve was generated by raising the temperature from 65° C. to 95° C. at a rate of 0.1° C./s, with constant measurement of fluorescence, followed by cooling at 40° C. for 30 seconds. Relative gene expression was quantified using the 2-ΔΔCT method.

(6) Colony Forming Unit Assay

For colonies, three different concentrations ($2 \times 10^5$, $1 \times 10^5$, $0.5 \times 10^5$ cells/ml) of HTSCs and BM-MSCs were placed into culture flasks containing NH CFU-F medium (Miltenyi Biotec, Bergisch Gladbach, Germany). On day 14, cells were fixed with methanol and dried. The cells were then stained using Giemsa staining solution (Sigma-Aldrich) and incubated for 5 minutes at room temperature. After washing and drying, colonies between 1 and 8 mm in diameter (more than 20 cells) were counted.

(7) Teratoma Formation in Immunodeficient Mice

To analyze tumor growth, undifferentiated HTSCs were resuspended in PBS ($1 \times 10^6$ cells/20 μl) and injected into kidney capsules and testicles of immunodeficient SCID mice. As a positive control for teratoma formation, human ESCs (CHA-hESC35: hES12012006, Korea Stem Cell Registry, KNIH, Osong, Republic of Korea) were injected into testicles of immunodeficient SCID mouse. After 12 to 16 weeks to allow tumor formation, mice were euthanized. Teratoma tissues were placed in 4% PFA and then embedded in paraffin. Tissue sections were stained with hematoxylin and eosin (Sigma) for histological examination. To identify human cells in the mouse tissue, we performed immunohistochemistry using a human-specific antibody (Stem-121™, Stem Cells Inc., Cambridge, UK) in SCID mouse testis with or without HTSC injection.

(8) In Vitro Differentiation into Adipogenic, Osteogenic, and Chondrogenic Cells HTSCs were collected at p5, p13 and p20 and resorted HTSCs were also collected at p20. As controls, hESCs at p72 and BM-MSCs at p3 were also collected to analyze their differentiation potential into the 3 germ cell layers. All types of cells were resuspended and replated into 6-well culture dishes. After 24 hours, the non-adherent cells were removed by replacing the medium, and the attached cells were cultured until confluence. The cells were then grown for 21 days in adipogenic, osteogenic, and chondrogenic medium (Invitrogen). Adipogenic differentiation was visualized using Oil Red O (Sigma-Aldrich) staining. The expression of adipogenesis-specific genes (PPARγ and C/EBPα) was analyzed by real-time RT-PCR. Osteogenic differentiation was visualized by Alizarin Red S (Sigma-Aldrich) staining and analyzed by osteogenesis-specific gene (COL I and CBFA I) expression. Chondrogenic differentiation was visualized by Alcian blue (Sigma-Aldrich) staining and analyzed by chondrogenesis-specific gene (COMP and SOX9) expression.

(9) In Vitro Differentiation into Neurogenic Cells

Neurogenic differentiation of HTSCs and BM-MSCs was induced in DMEM-F12 medium (Gibco) with N2 supplement (Gibco), 2 mM L-glutamine (Gibco) and penicillin/streptomycin solution (1×, Gibco). After 3 days, cells were fixed and processed for immunocytochemistry. After the cell clumps formed floating spherical cells resembling neurospheres, cells ($1 \times 10^6$ cells/ml) were detached; re-plated on fibronectin (10 μg/ml, Sigma)-coated dishes; cultured in Neural Progenitor Basal Medium (NPBM, Cambrex, One Meadowlands Plaza, NJ) supplemented with 2 mM L-glutamine, ng/ml epidermal growth factor (EGF, Invitrogen), 10 ng/ml bFGF and penicillin/streptomycin solution for 3 days. Growth factors were added every day. Induction of terminal neural differentiation was initiated by plating cells in Neurobasal Medium (Gibco) supplemented with 0.5 μM all-trans-retinoic acid (Sigma), 1% FBS (Gibco), 5% horse serum (Gibco), 1% N2 supplement, and penicillin/streptomycin solution. Cells were differentiated for 10-14 days. Neurogenic differentiation was observed using microscopy and confirmed by RT-PCR.

(10) In Vitro Differentiation of HTSC into Insulin-Secreting Cells

Differentiation into insulin-secreting cells was induced according to the manufacturer's instructions for the specific medium (Bcell Bio, Seoul, Korea) (Kang, H. M., et al. Insulin-secreting cells from human eyelid-derived stem cells alleviate type I diabetes in immunocompetent mice. *Stem Cells* 27, 1999-2008 (2009)). Differentiation efficiency was analyzed by measuring insulin and C-peptide secretion into the culture medium. In brief, cells were treated with low-glucose (5.5 mM) DMEM containing 0.5% BSA for 12 hours, and then stimulated by high glucose (25 mM)-DMEM for 2 hours at 37° C. The amounts of insulin and C-peptide released into the medium were measured with human insulin and C-peptide enzyme-linked immunosorbent assay (ELISA) kits (Mercodia, Winston Salem, N.C.) according to the manufacturer's instructions. Synthesis of insulin and C-peptide mRNAs in differentiated cells was confirmed by RT-PCR.

(11) In Vivo Differentiation into Adipogenic, Osteogenic, and Chondrogenic Cells The animal experiments concerning mouse handling were approved by the Institutional Animal Care and Use Committee of CHA University. BALB/c female mice (6 weeks old) were divided into 4 groups. The dextran (DEX)-loaded microspheres (30 mg) harboring HTSCs were implanted subcutaneously into the backs of 12 nude mice. In group I, the control group (n=3), DEX-loaded microspheres were injected into the back subcutis of female mice. In group II (n=3), 100 ng/ml TGβ3-coated microspheres were injected into the back subcutis of female mice. In group III (n=3), 100 ng/ml BMP2-coated microspheres were carefully injected into the back subcutis of female mice. In group IV (n=3), 50 ng/ml IGF and bFGF (Invitrogen)-coated microspheres were injected into the back subcutis of female mice. At 4 weeks post-treatment, the female mice were euthanized via an overdose injection of anesthetic (ketamin), and the skin surrounding the injection site ($2 \times 2$ cm$^2$) was carefully excised for subsequent biological examination. Tissues were harvested and processed for RT-PCR, immunoblotting, immunocytochemistry and immunohistochemistry to confirm in vivo differentiation.

(12) Transplanted HTSCs into Bilateral Cavernous Nerve Crush Injury (BCNCI) Rat Model Thirty-two 12-week-old male Sprague-Dawley rats were randomly divided into four groups (eight rats per group) as follows: 1) only laparotomy (sham group); 2) bilateral cavernous nerve crush injury (BCNCI) and 0.1 mol/L phosphate-buffered saline instillation (Injury group); 3) BCNCI and periprostatic BM-MSC instillation, $1 \times 10^7$ stem cells suspended in 100 μl sterile PBS (BM group); and 4) BCNCI and periprostatic HTSC instillation, $1 \times 10^7$ stem cells suspended in 100 μl sterile PBS (HTSC group). Before injection, the stem cells were labeled with CellTracker™ CM-Dil (C7000, Invitrogen) for stem cell tracking.

Figure 7A:
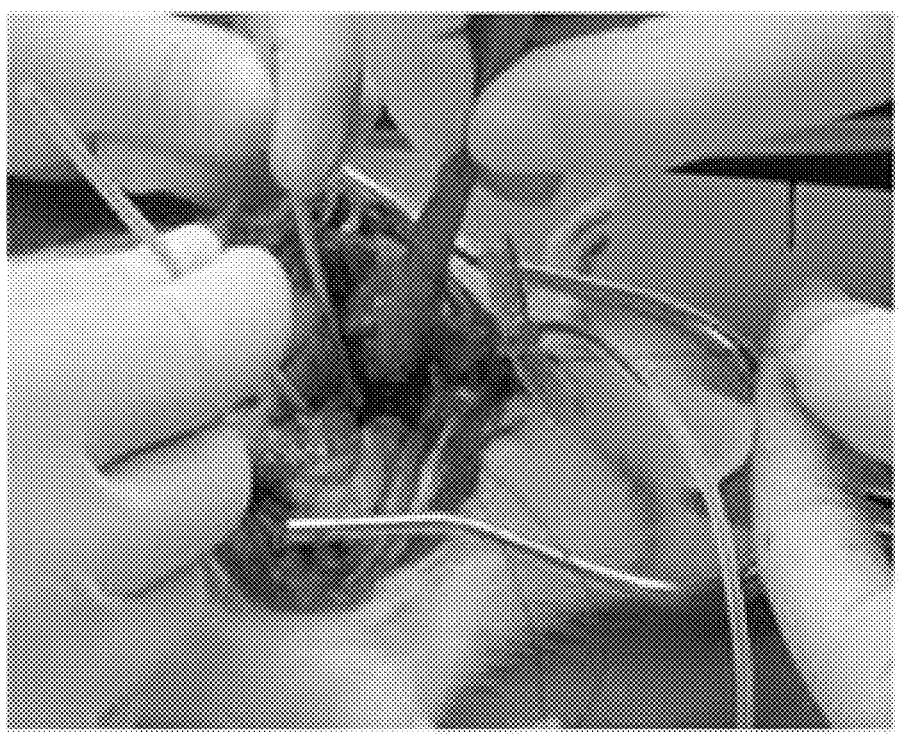
FIG. 7a shows cavernous nerve electrostimulation proximal to the site of injury in a rat, in which the corpus cavernosum was cannulated using a 24-gauge needle.

Four weeks following implantation, erectile function was assessed by cavernous nerve electrostimulation (3V, 0.2 ms, 20 Hz) proximal to the site of injury (FIG. 7a). Systemic mean arterial pressure (MAP) and intracavernosal pressure (ICP) were recorded and analyzed electronically (Powerlab, AD Instruments, Colorado Springs, Colo., USA, FIG. 7b). The ICP/MAP ratio was compared among the groups. After the functional evaluation, the prostate lobes of each rat were harvested. Nuclear and neural staining were performed with hematoxylin and nestin antibody (Santa Cruz Biotechnology). Also, we performed additional immunohistochemistry using a human-specific antibody (Stem-121™) and the neuron-specific β-tubulin class III (TuJI, Santa Cruz Biotechnology) in the crush injury area of each mouse.

(12) Statistical Analysis

All experiments were replicated at least 3 times, and data are presented as the means±SEMs. The differences among groups were analyzed with ANOVA. A p value <0.05 was considered statistically significant. Correlations between CD34 expression and genes specific to the three germ layer lineages were analyzed using Pearson's coefficient of correlation.

2. Results (1) Isolation and Expansion of Human HTSCs

The mean age of the 15 donors was 36.7±6.7 years (between 29 and 55 years). In human testis tissues, CD34-positive cells were distributed predominantly in the seminiferous tubules and between tubules. Expression of CD31 was localized in only the blood vessel and αSMA was in only the tubules (FIG. 1). Moreover, the expression pattern of CD34, CD73, CD31, and αSMC was very similar in the testis between OA and NOA patients. However, CD73 was not expressed in the basal lamina of the seminiferous tubules, although their numbers were quite small. Additionally any CD34/CD31-double-positive cells were not observed in the testes. To localize CD34/CD73-double-positive cells in human testis, cryosections of biopsied seminiferous tubules were prepared and stained with CD34 and CD73 antibodies. The CD34/CD73-double-positive cells were localized outside of the tubules (in interstitial cells) and distributed broadly but there was a small number of them (FIG. 1).

Figure 2A:
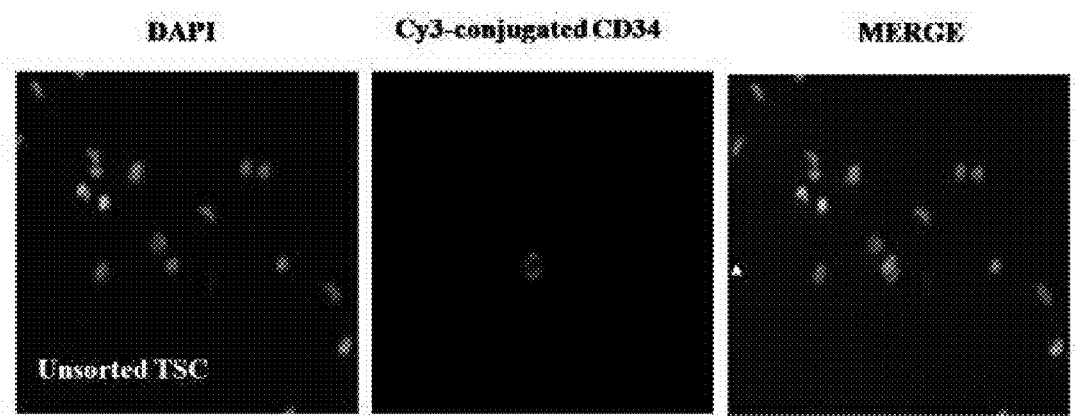
FIG. 2a is the result of immunocytochemistry analysis, which reveals expression of CD34 in human TSCs (100×). The red signal is CD34 expression.
Figure 3A:
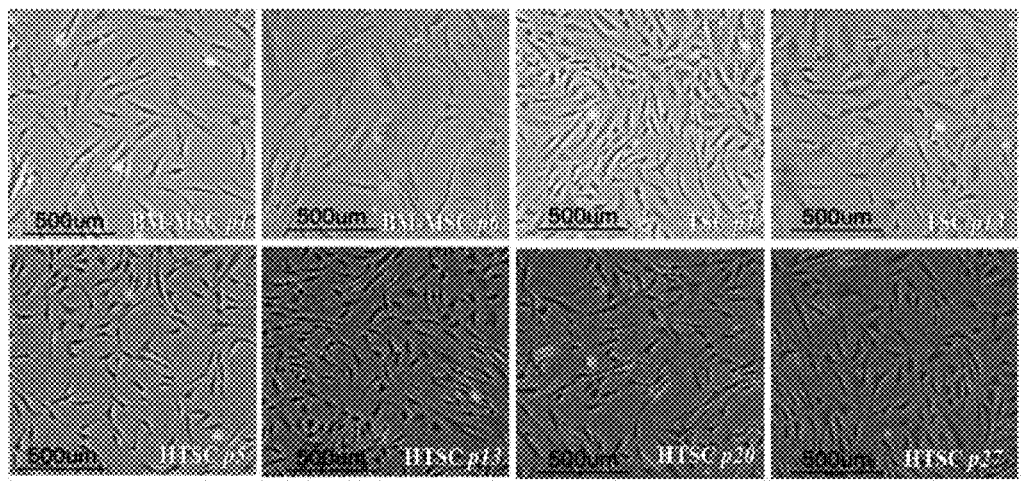
FIG. 3a is phase contract images, which exhibit differences in morphology of cells maintained under the same culture conditions (MSC-like vs. senescent-like morphology), i.e., bone marrow-derived mesenchymal stem cells (BM-MSCs) at p1 and p6, human TSCs at p1 and p13, and highly proliferative testis-derived stem cells (HTSCs) at p5, p13, p20, and 27.
Figure 3B:
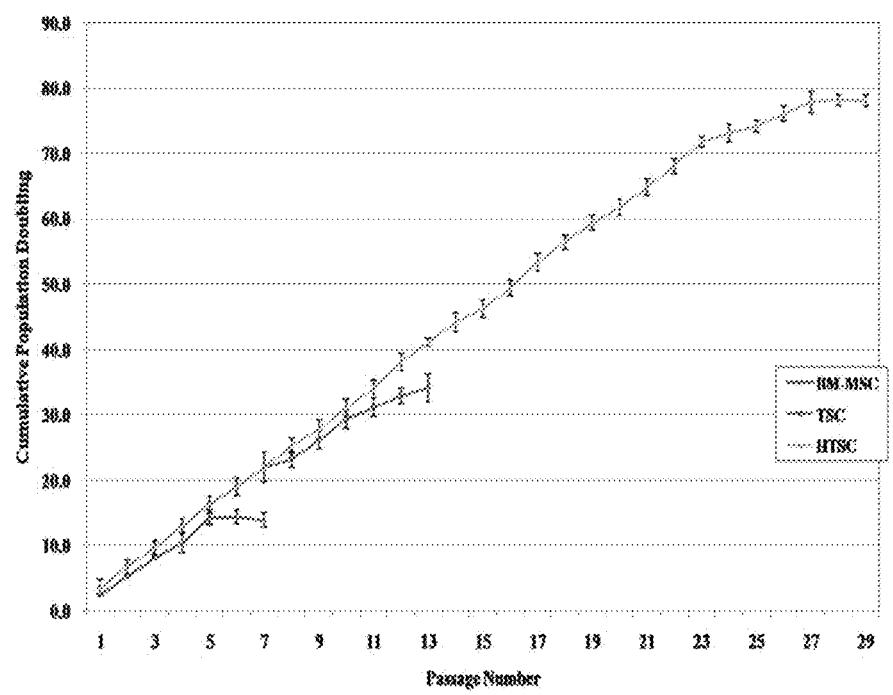
FIG. 3b shows comparison between cumulative doubling number of BM-MSCs, TSCs, and HTSCs.
Figure 9A:
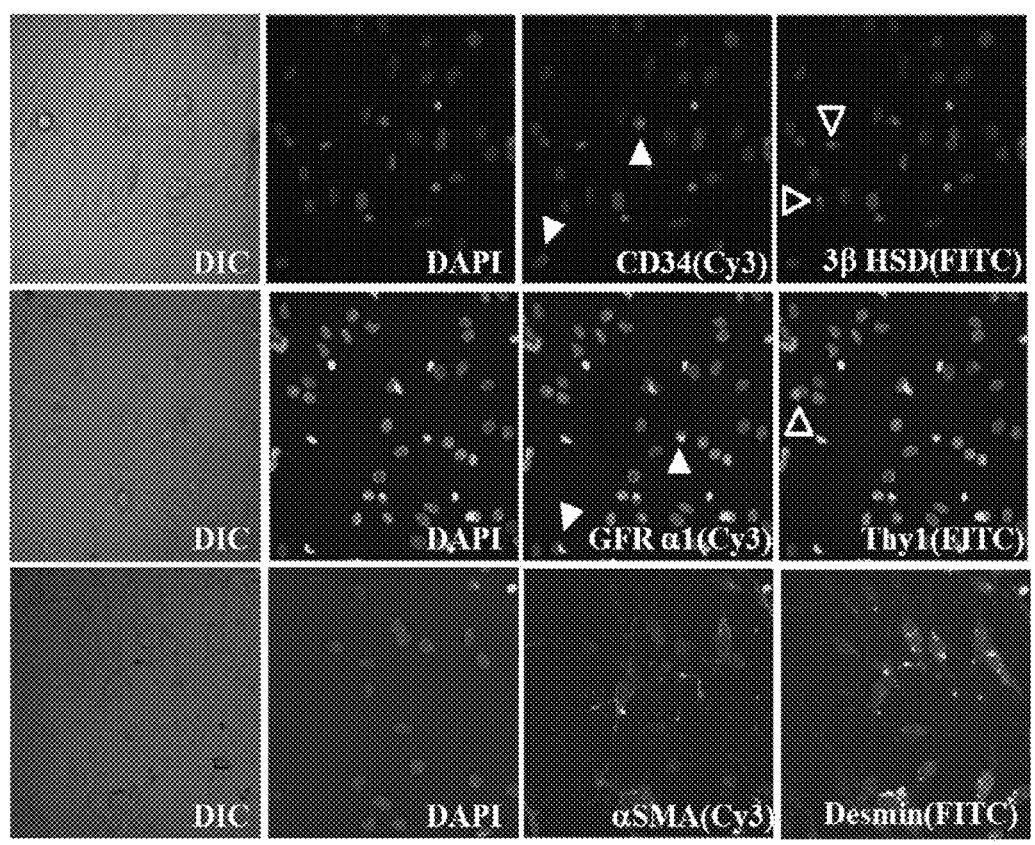
FIG. 9a shows specific marker expression in primary testis peritubular cells. Immunocytochemistry analysis reveals expression of CD34 (red, white arrowheads) and 3β-HSD (green, open arrowheads) in the first row, GFR α1 (red, white arrowheads) and Thy-1 (green, open arrowheads) in the second row, and αSMA (red) and Desmin (green) in the third row.

Collected interstitial cells were primarily cultured for 2-3 passages (FIG. 9a). Upon culturing in vitro, adherent cells isolated from human testicular seminiferous tubules were sorted by CD73. These cells had a MSC-like morphology and expressed CD73 antigen constitutively; thus, we herein referred to them as testis-derived stem cells (TSCs). TSCs included two sub-populations of cells (CD34-negative and CD34-positive). The CD34-positive TSCs were re-isolated using magnetic-activated cell sorting (MACS), and then replated onto separate culture dishes. Because of the very small number of CD34-positive cells among the CD73-sorted TSCs (FIG. 2a), the number of cells positive for CD34/CD73 co-expression was significantly smaller (approximately 1,000 cells [0.02%] from 100 mg of biopsied tissue) than that of CD34-negative TSCs. Additionally, because of their initial small number, the CD34/CD73-double-positive cells only reached 80% confluency after 14 days in culture, which represents passage 1 (p1) of these cells. Yet, once they expanded further, the CD34/CD73-double-positive cells exhibited a high proliferative activity; thus they are herein referred to as HTSCs (high proliferative-TSCs). Cells were fed every 3-4 days with fresh medium, and they maintained MSC-like morphology until p26 or 27 (FIG. 3). In contrast, BM-MSCs and TSCs maintained a MSC-like morphology until p6 and p13, respectively, and then showed a senescent morphology (gross enlargement and flattening of cells, FIG. 3a). Throughout the culturing, CD34-negative/CD73-positive TSCs underwent an average of 34.3±2.1 population doublings, and the total number of these cells recovered per patient was $2.2 \times 10^{13}$ cells. In contrast, HTSCs underwent an average of 67.3±2.1 population doublings, and the total number of cells recovered was $5.6 \times 10^{16}$ per patient (FIG. 3b).

(2) Characterization of HTSCs (CD34/CD73-Double-Positive TSCs)

Figure 10:
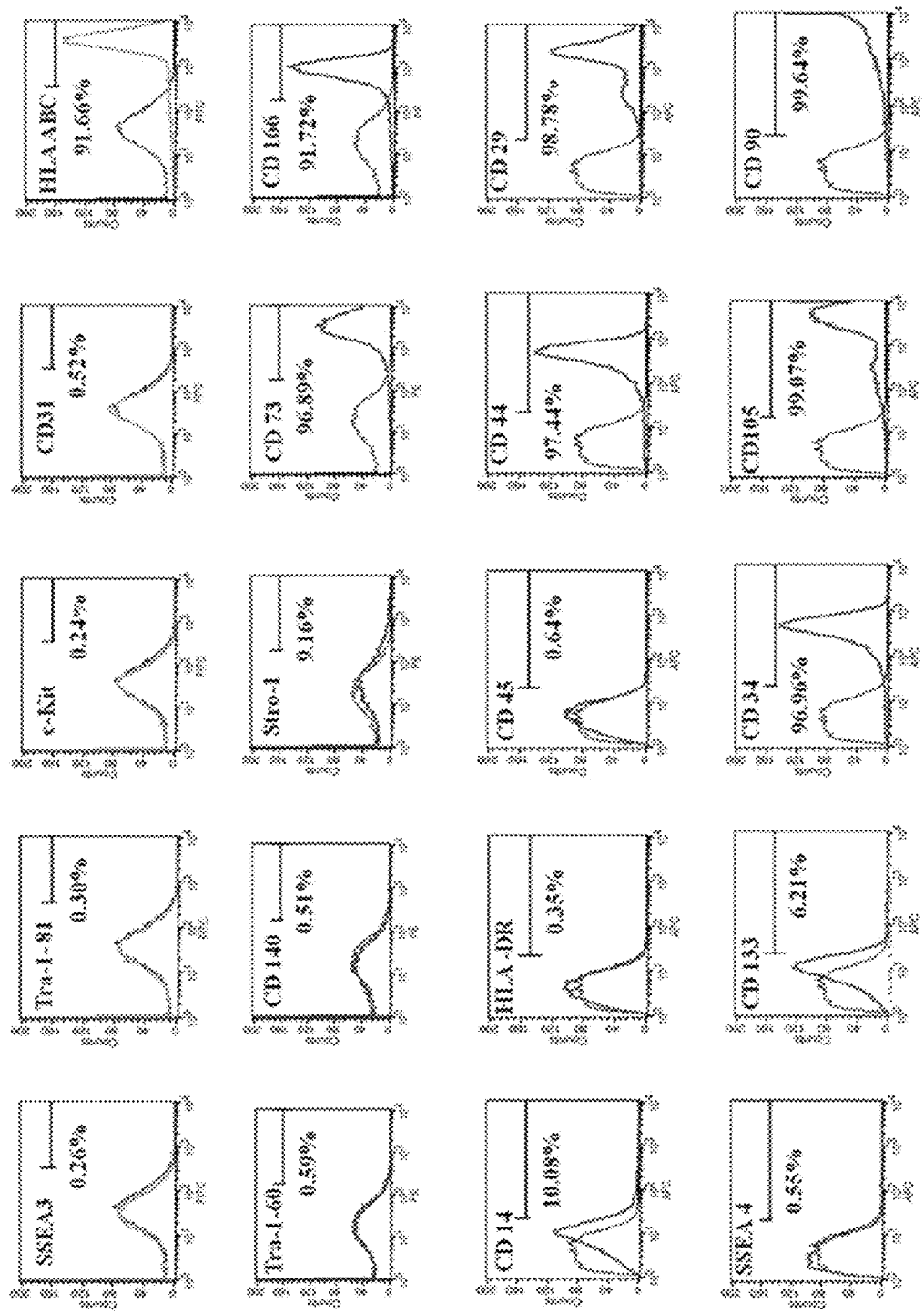
FIG. 10 shows the results of flow-cytometric analyses of highly proliferative testis-derived stem cells (HTSCs). HTSCs were strongly positive for HLA-ABC, CD73, CD166, CD44, CD29, CD90, CD105 and CD34, weakly positive for CD14, CD133, and Stro-I, and negative for SSEA3, TRA-1-81, c-Kit, CD31, TRA-1-60, CD140, HLA-DR, CD45 and SSEA4 antigens. Abbreviations: APC, allophycocyanin; FITC, fluorescein isothiocyanate; PE, phycoerythrin.

To characterize HTSCs, we performed flow cytometry, immunocytochemistry, and RT-PCR. At p3 after sorting, multi-color flow cytometry was performed using various markers. The HTSCs were strongly positive for CD34 (96.5%±3.5), CD73 (95.6%±1.5), class I major histocompatibility (MHC) antigens (HLA ABC), CD29, CD44, CD90, CD105, and CD166; were weakly positive for CD14, CD133, and Stro-I, and were negative for CD31, CD45, HLA DR, TRA-1-60, SSEA3, SSEA4, TRA-1-81, c-Kit, and CD140 (FIG. 10).

Figure 2B:
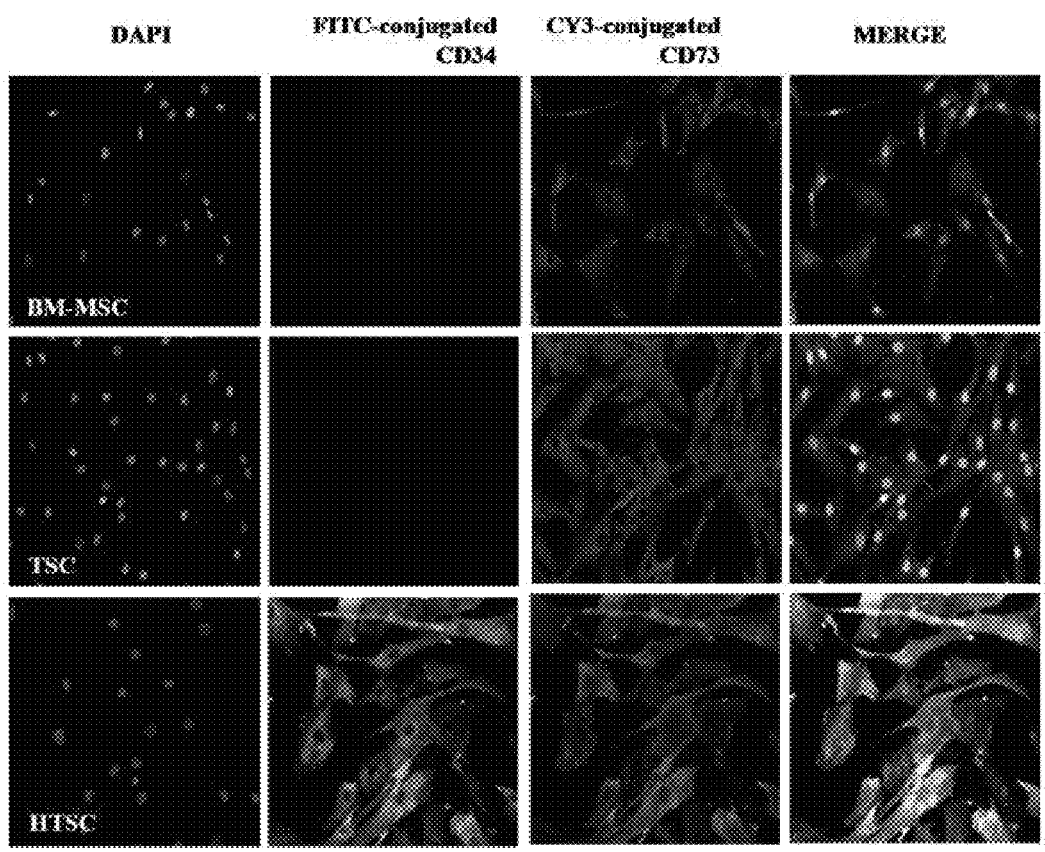
FIG. 2b is the result of immunocytochemistry analysis which shows expression of CD34 and CD73 in BM-MSCs, TSCs, and HTSCs. DAPI nuclear staining is in blue.

Immunocytochemical analysis confirmed that HTSCs co-expressed CD34 and CD73, but TSCs and BM-MSCs expressed only CD73 and not CD34 (FIG. 2b). Also confirming our flow cytometry results, HTSCs did not express any of the pluripotency markers c-Kit, TRA-1-60, TRA-1-81, SSEA3 and SSEA4, nor did they express OCT4 (FIG. 2c).

Figure 9C:
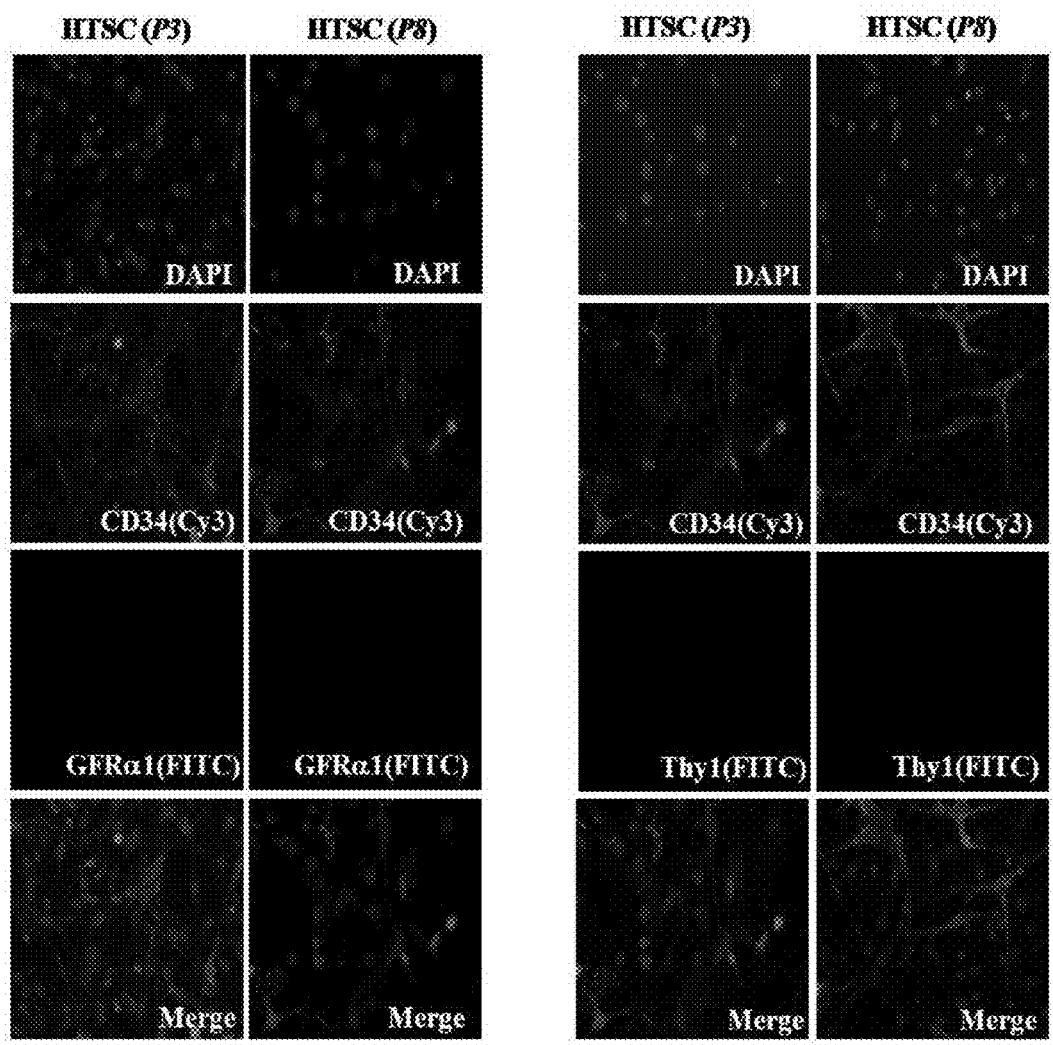
FIG. 9c shows specific marker expression in highly proliferative testis-derived stem cells (HTSCs) at p3 and p8. Immunocytochemistry analysis reveals expression of CD34 (red) and no expression of GFR al or Thy-1 (green).
Figure 9D:
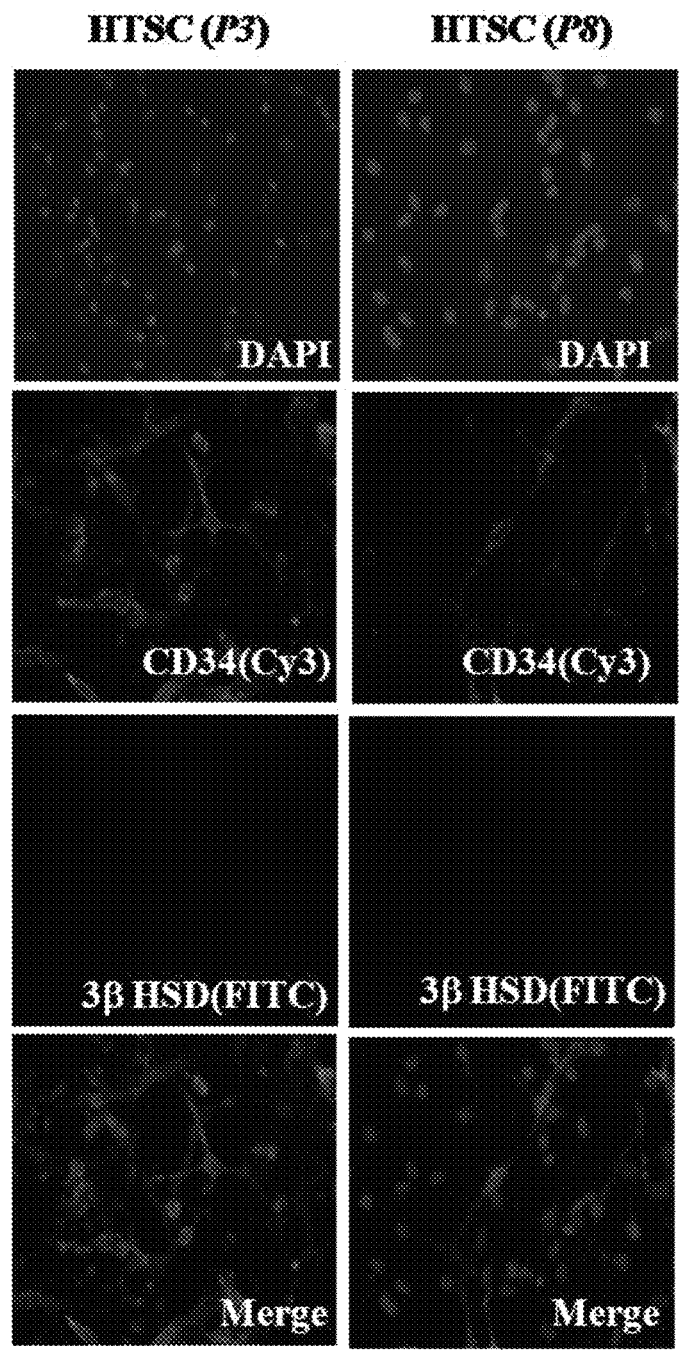
FIG. 9d shows the results of immunocytochemistry analysis which reveals expression of CD34 (red) and no expression of 3β-HSD.
Figure 9E:
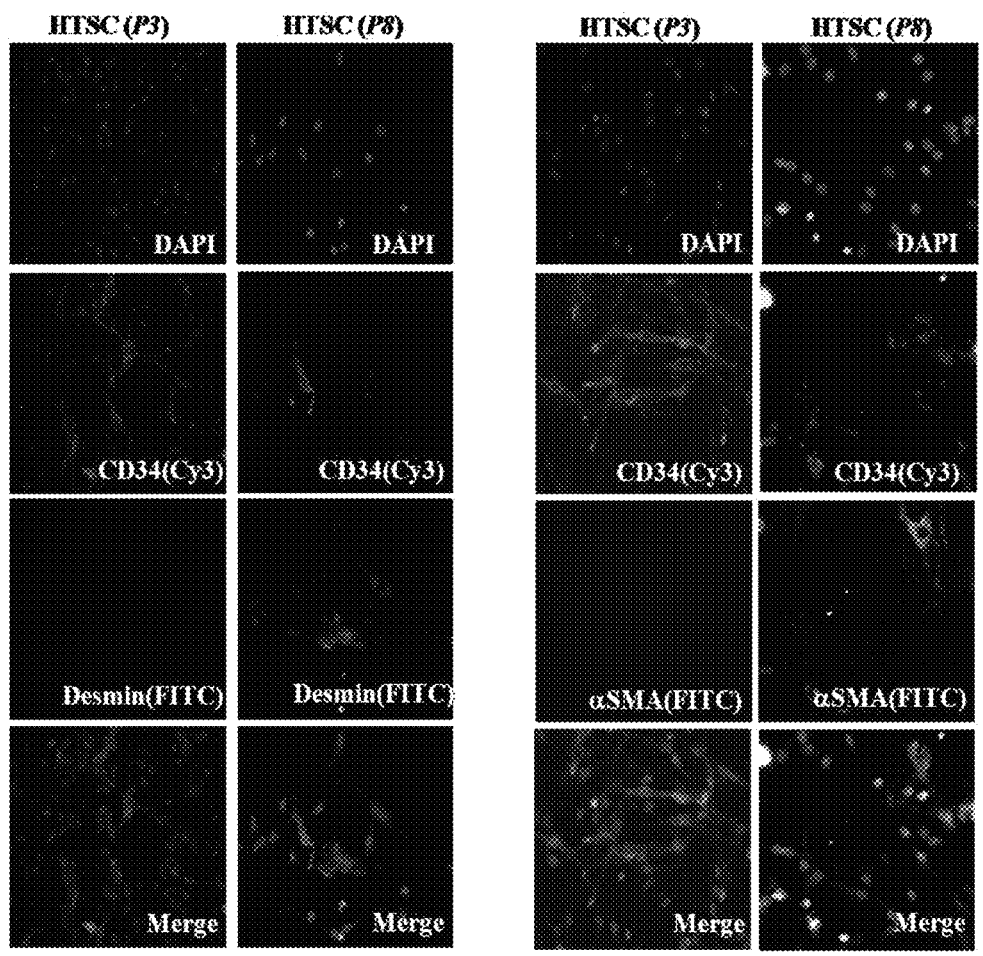
FIG. 9e shows the results of immunocytochemistry analysis which reveals expression of CD34 (red) and Desmin or αSMA.

To analyze the contamination of germ cells and other somatic cells, HTSCs were analyzed by immunocytochemistry using germ cell markers (GFR α1 and Thy-1), a Leydig cell marker (3β-HSD), and peritubular myoid cell markers (Desmin and αSMC). As shown in FIG. 9a, a small number of CD34-positive cells existed among the primary cultured cells that included various somatic cells. After sorting by CD73 and CD34, most cells expressed CD34 at p3 and did not express markers for germ cells or testicular somatic cells. At p8 after sorting, the number of CD34-positive cells had decreased significantly. Markers for germ cells and Leydig cells were still not detected, but signals for Desmin and αSMC re-appeared in a small number of CD34-negative cells (FIG. 9b to FIG. 9d).

Figure 11A:
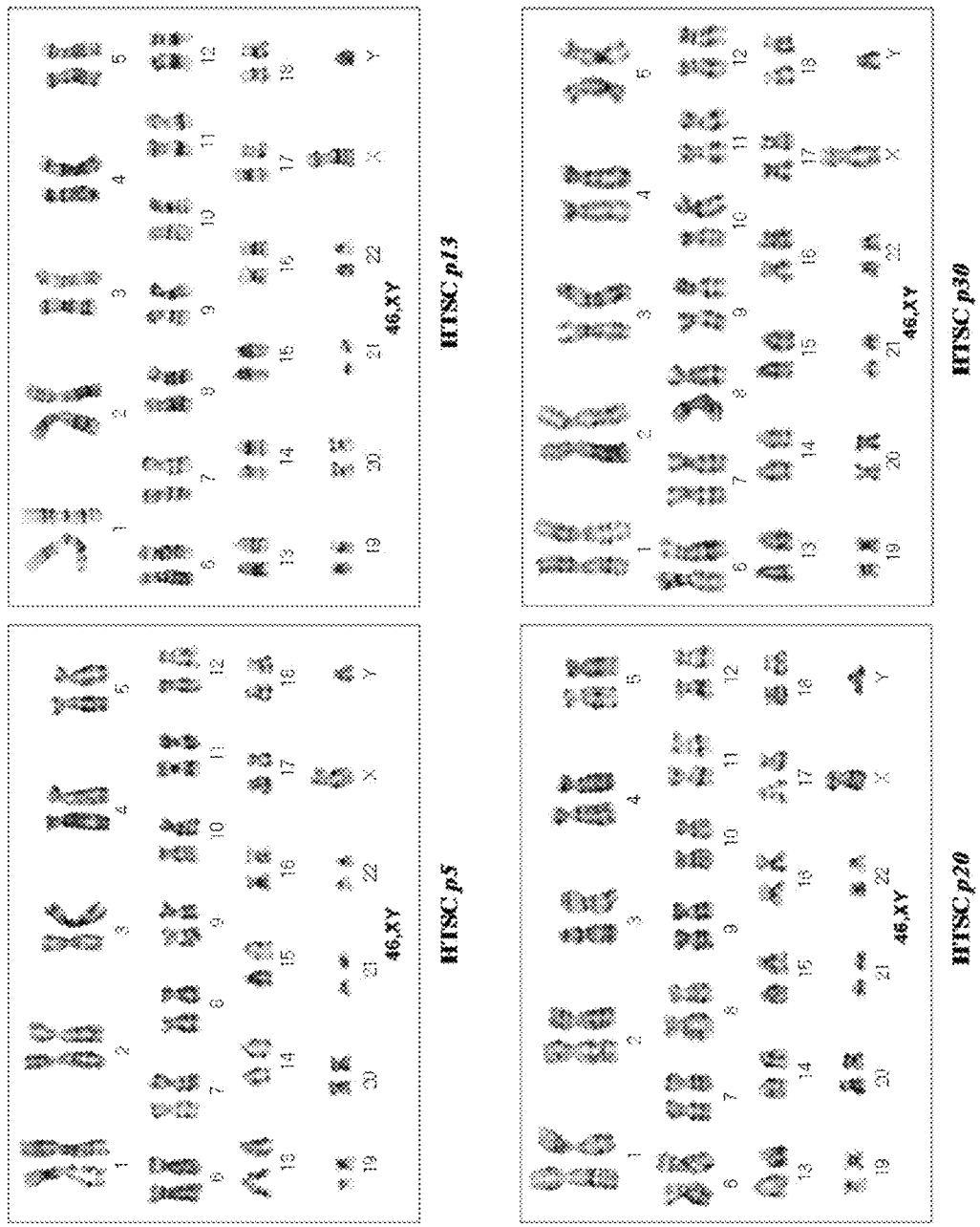
FIG. 11a shows that HTSCs have a normal karyotype (2n, 46XY) at the indicated passages.
Figure 11B:
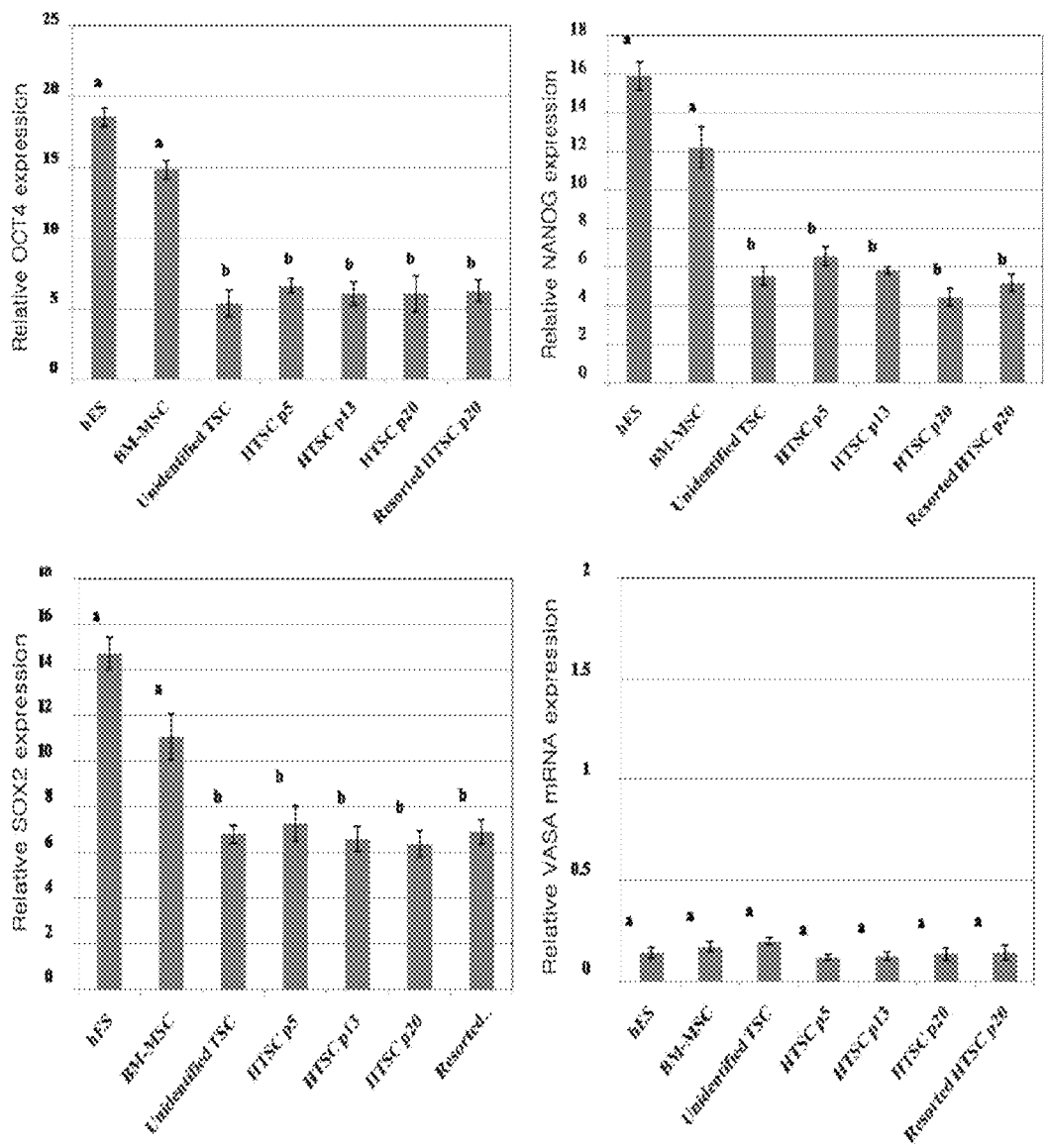
FIG. 11b shows the results of RT-PCR analysis of pluripotency (OCT4, NANOG, SOX2) and germ cell (VASA) markers in HTSCs.

To analyze the genetic stability of HTSCs during long-term propagation in vitro, we performed karyotyping analysis at p5, p13, p20 and p30, which consistently showed normal diploid karyotypes (46, XY) without chromosomal aberrations (FIG. 11a). RT-PCR analysis also demonstrated that HTSCs expressed only low levels of the pluripotency-related OCT4, SOX2, and NANOG genes, and did not express the germ cell-specific VASA mRNA at p5, p13 or p20 (FIG. 11b).

Figure 12:
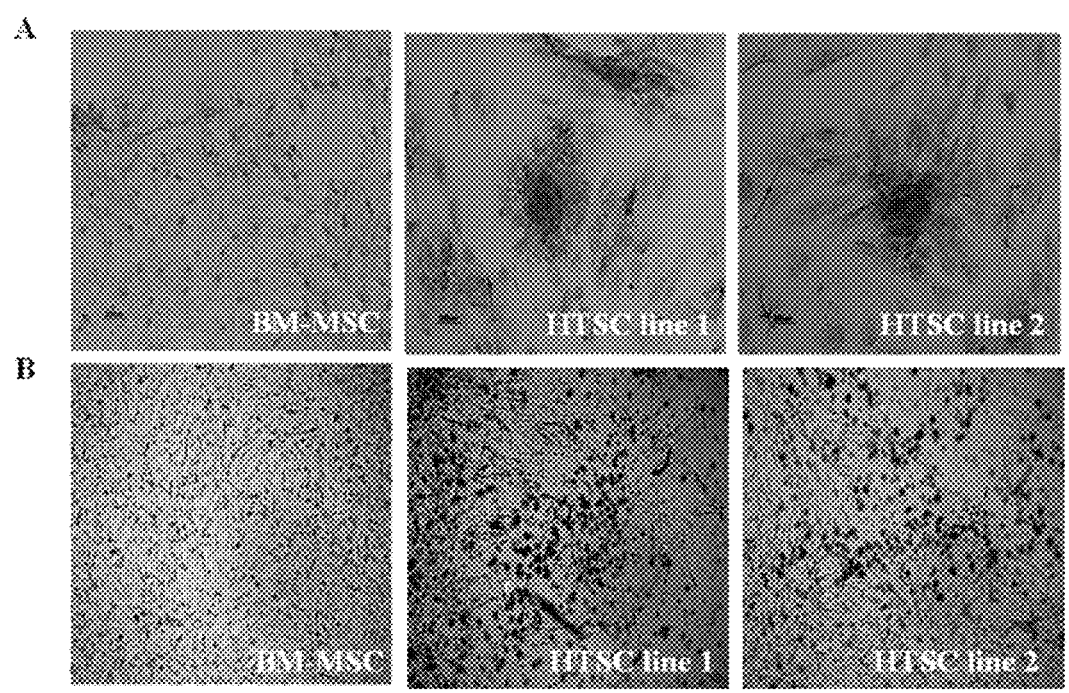
FIG. 12 shows the results of colony-forming unit assays for bone marrow-derived mesenchymal stem cells (BM-MSCs) and highly proliferative testis-derived stem cells (HTSCs). BM-MSCs and HTSCs show colony-forming events when grown under non-hematopoietic conditions (A) but do not form colonies when grown under hematopoietic conditions (B).
Figure 13A:
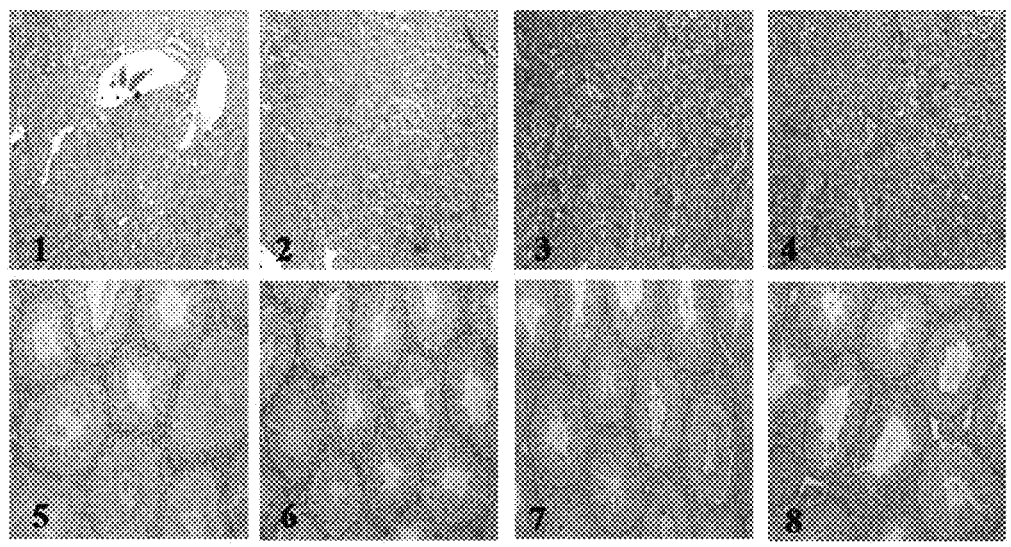
FIG. 13a shows the results of teratoma formation assays for human highly proliferative testicular stem cells (HTSCs) in kidney (A1-A4) and testis (A5-A8) (100×). There was no teratoma formation in either tissue.
Figure 13B:
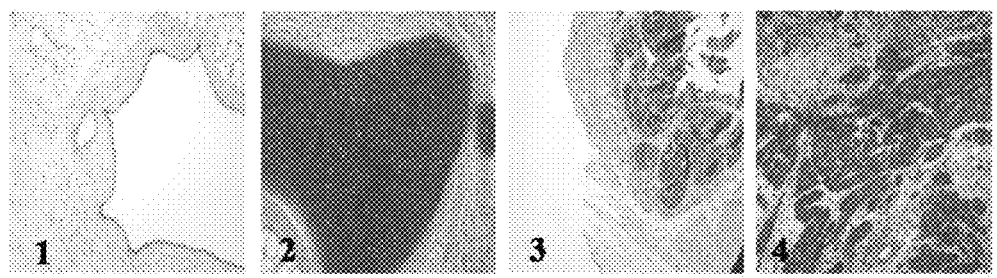
FIG. 13b shows teratoma formation from embryonic stem cells (×200). Gut-like epithelium (endoderm, H-E staining, B1), cartilage (mesoderm, Alcian blue staining, B2), secretory epithelium (ectoderm, PAS staining, B3), and muscle fibers (mesoderm, Masson's trichrome staining, B4).
Figure 13C:
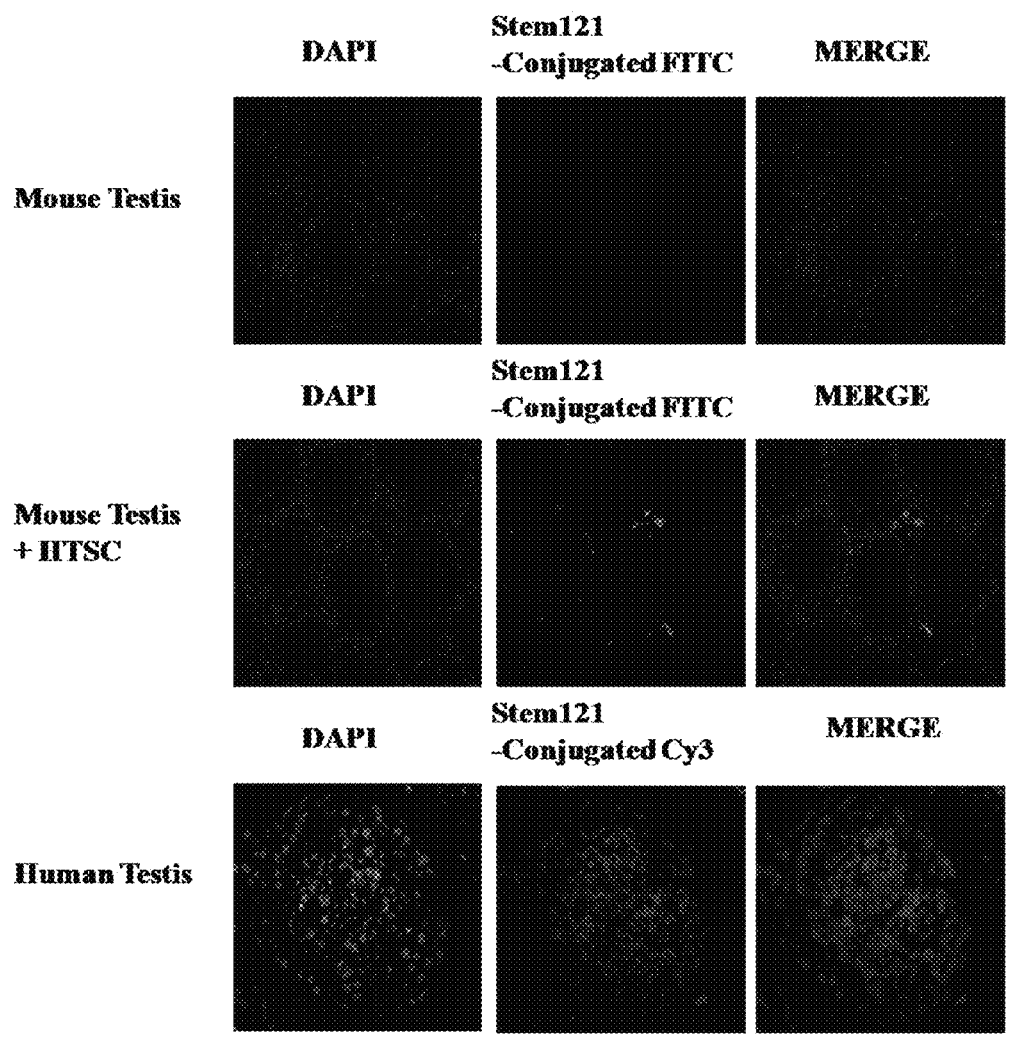
FIG. 13c shows specific human cell-specific marker (Stem 121) expression in mouse and human testis tissues. Immunocytochemistry analysis reveals no expression of Stem 121 in the first row and but expression in the second and third rows.

To determine if they displayed other typical characteristics of stem cells, the isolated HTSCs were plated for colony-forming assays, and the results were compared with those of BM-MSCs. The HTSCs formed typical stem cell colonies, and their efficiency of colony formation was significantly higher than that of BM-MSCs (15.2±2.1% vs. 1.0±0.1%, FIG. 12a). However, colonies of hematopoietic cells were not observed for either type of stem cells (FIG. 12b). To examine their tumorigenic potential, HTSC lines were injected into the kidney capsules and testicles of SCID mice. By 12-16 weeks after injection, none of the HTSC lines had formed tumors in any of the 10 recipient SCID mice, even though small numbers of injected human HTSCs (Stem-121™-positive cells) remained in the testis (FIG. 13).

Figure 4A:
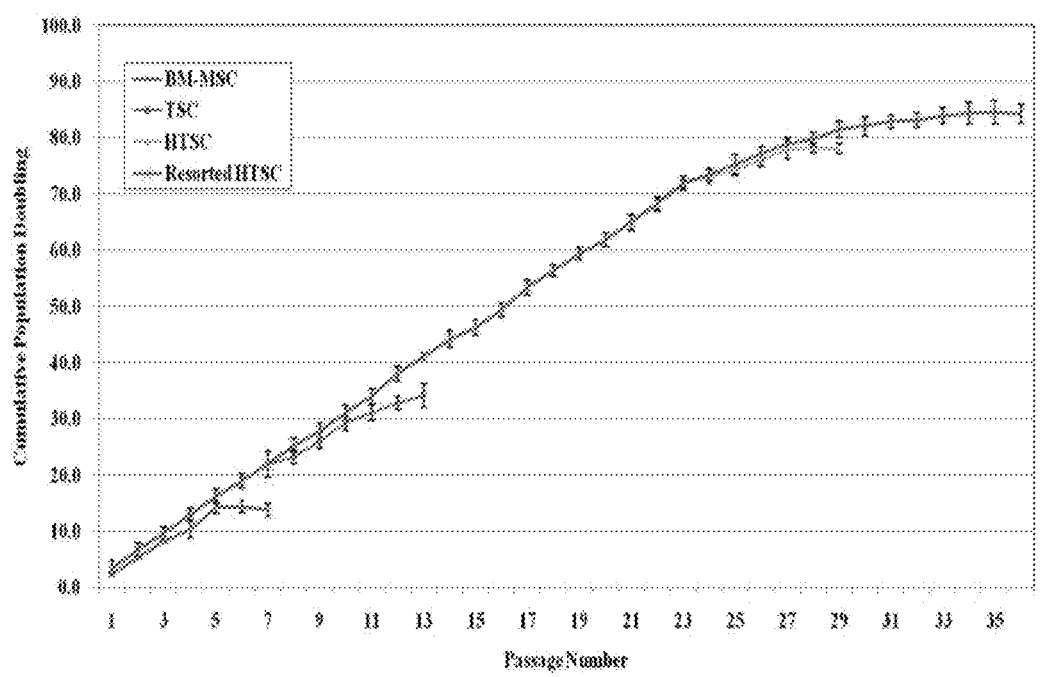
FIG. 4a shows comparison of cumulative doubling number of bone marrow-derived mesenchymal stem cells (BM-MSCs), testis-derived stem cells (TSCs), highly proliferative testis-derived stem cells (HTSCs) and resorted HTSCs.
Figure 4B:
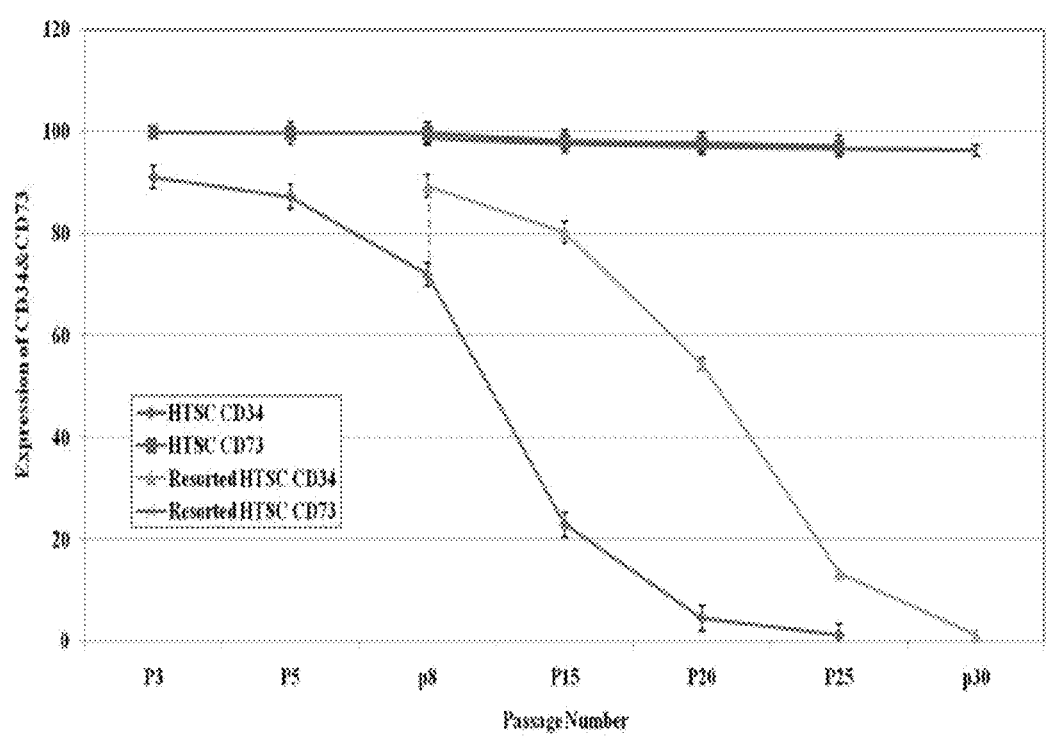
FIG. 4b shows that, after further culturing of HTSCs, the population of CD34-positive cells was reduced, but CD73-positive cells remained abundant.
Figure 4C:
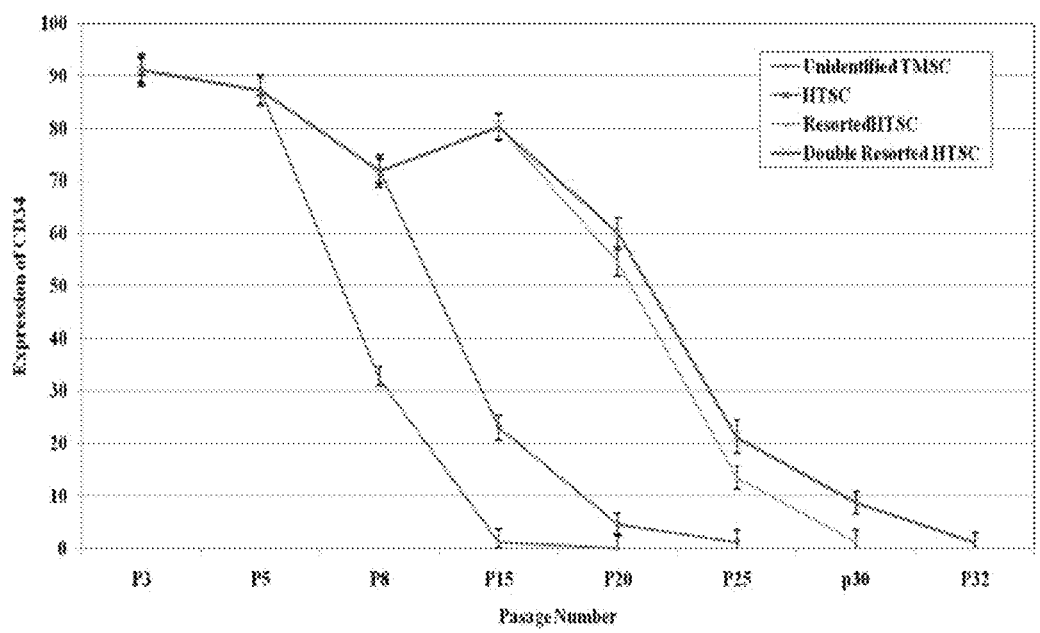
FIG. 4c shows that, during culture, HTSCs lost CD34 expression steadily and did not regain it; but that proliferation of HTSCs was extended further when the sub-population of CD34-positive cells was isolated by MACS and replated.

(3) Changes in CD34 Expression During Long-Term Culture and Population Recovery by Resorting We analyzed the population of CD34-positive cells during long-term culture of HTSCs. The proportion of CD34-positive cells decreased steadily over time as the culture continued (FIG. 4b). The population of CD34-positive cells was barely detectable when HTSCs reached passages 15-20. After this point, the cell doubling time increased, and their morphology also changed (FIG. 3a and FIG. 4a). At p8, HTSCs were resorted by MACS for CD34 (resorted HTSC) and their proliferation was analyzed. As shown in FIG. 4c, the population of CD34-positive cells in the resorted HTSCs was sustained for another 8 passages but decreased thereafter and they then proliferated until p30. When a subset of these resorted HTSCs were sorted again at p18 by CD34 (double re-resorted HTSCs), the proliferation of these double re-resorted HTSCs was maintained up to p36 (79.8±2.4 population doublings and $1.3 \times 10^{19}$ cells in double resorted HTSCs; 81.1±1.5 population doublings and $1.84 \times 10^{20}$ cells in re-resorted HTSCs) (FIG. 4c).

Figure 5A:
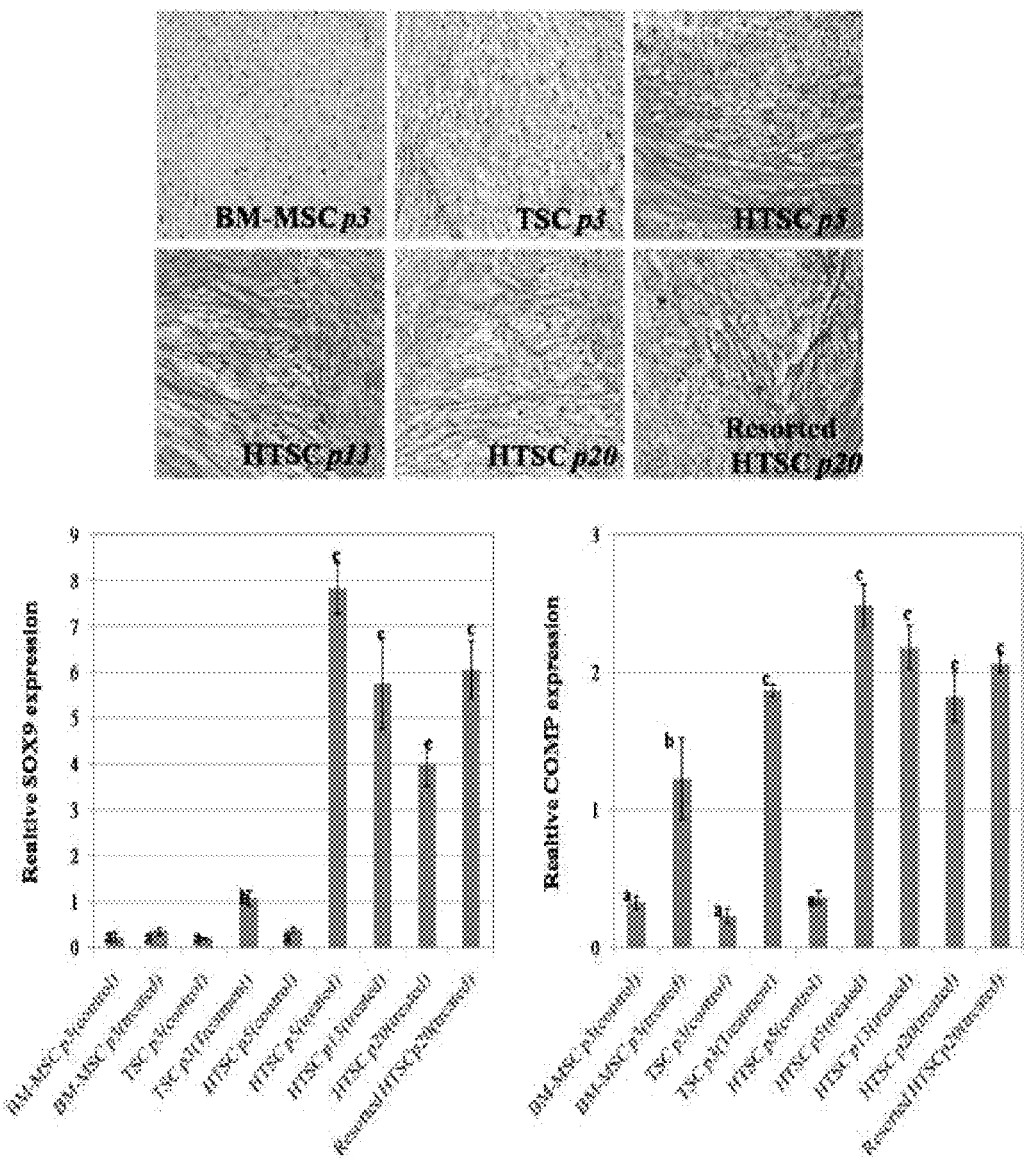
FIG. 5a shows staining with Alcian blue for sulfated proteoglycans (left panels) in BM-MSC at p5, TSCs at p3, and HTSCs at p5, p13, p20, and resorted p20 after chondrogenic differentiation for 3 weeks; and gene expression of SOX9 (the left of right panels) and COMP (the right of right panels) before and after chondrogenic differentiation was also analyzed in the same groups.

(4) In Vitro Differentiation into Chondrogenic, Adipogenic, and Osteogenic Cells HTSCs were collected at p5, p13 and p20 and resorted (p20; at p12 after sorting), and then they were differentiated in chondrogenic differentiation medium for three weeks. BM-MSCs at p3 and TSCs at p3 were used as experimental controls. Derivatives from all HTSCs, TSCs and BM-MSCs showed Alcian blue staining, indicative of polysaccharide production. However, mRNA levels of chondrogenic genes, COMP and SOX9 were significantly higher in HTSC-derived chondrogenic cells than in BM-MSC-derived chondrogenic cells (FIG. 5a). In HTSCs, COMP and SOX9 expression decreased but the culture continued but were maintained in the resorted HTSCs.

Figure 5B:
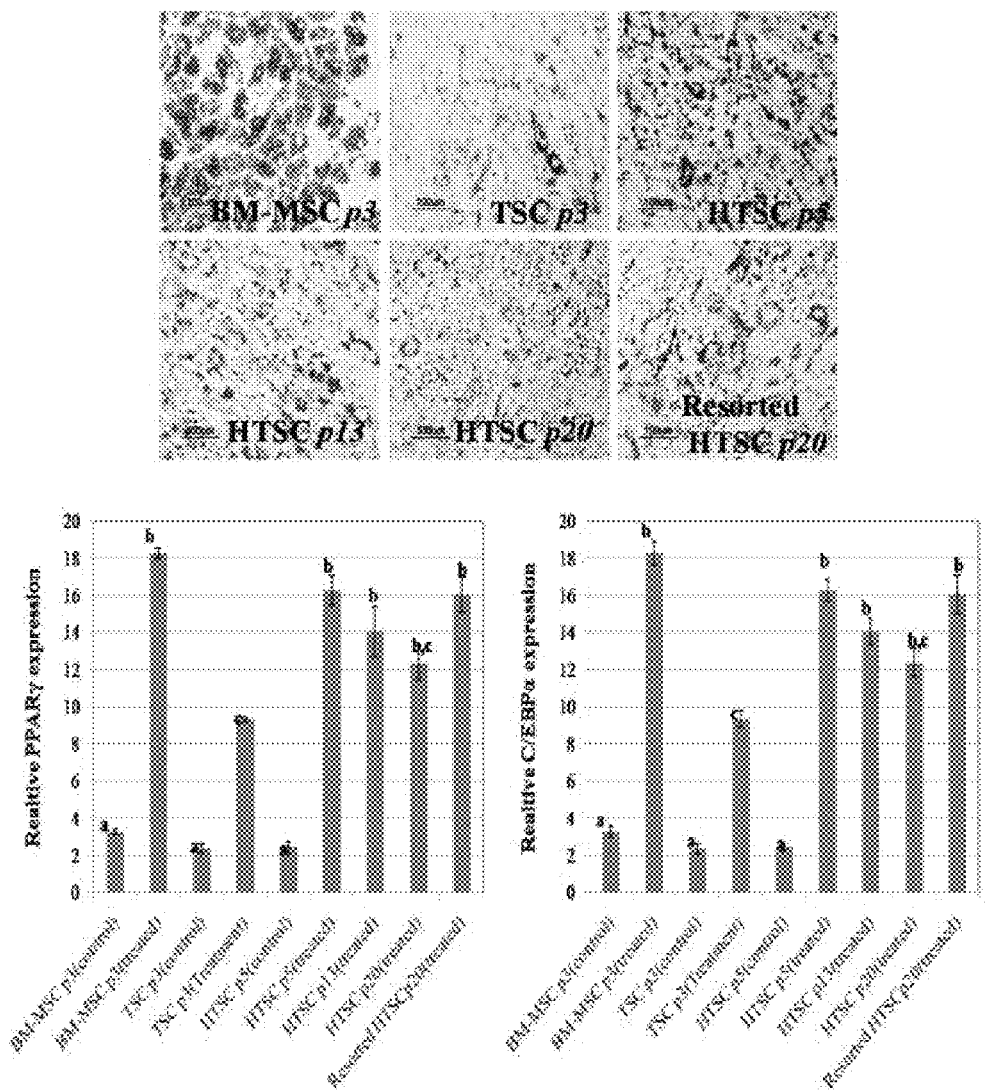
FIG. 5b shows staining of lipid droplets with Oil Red O (left panels) and gene expression of PPARγ (the left of right panels) and C/EBPα (the right of right panels).

To test their adipogenic capacity, the HTSCs were cultured in adipogenic medium for 3 weeks. BM-MSCs at p3 and TSCs at p3 were used as experimental controls. Under this condition, derivatives from HTSC-derived adipocytes showed a typical morphology of lipid-laden cells containing intracellular lipid droplets and stained positive for Oil red O. Adipogenically differentiated cells from BM-MSCs and from early passage of HTSCs exhibited similar expression levels of the adipogenic genes encoding PPARγ and C/EBPα (FIG. 5b). However, those gene levels were very low in TSCs. Gene expression levels of PPARγ and C/EBPα in HTSCs decreased steadily with continued culture but were maintained when the resorted HTSCs were differentiated.

Figure 5C:
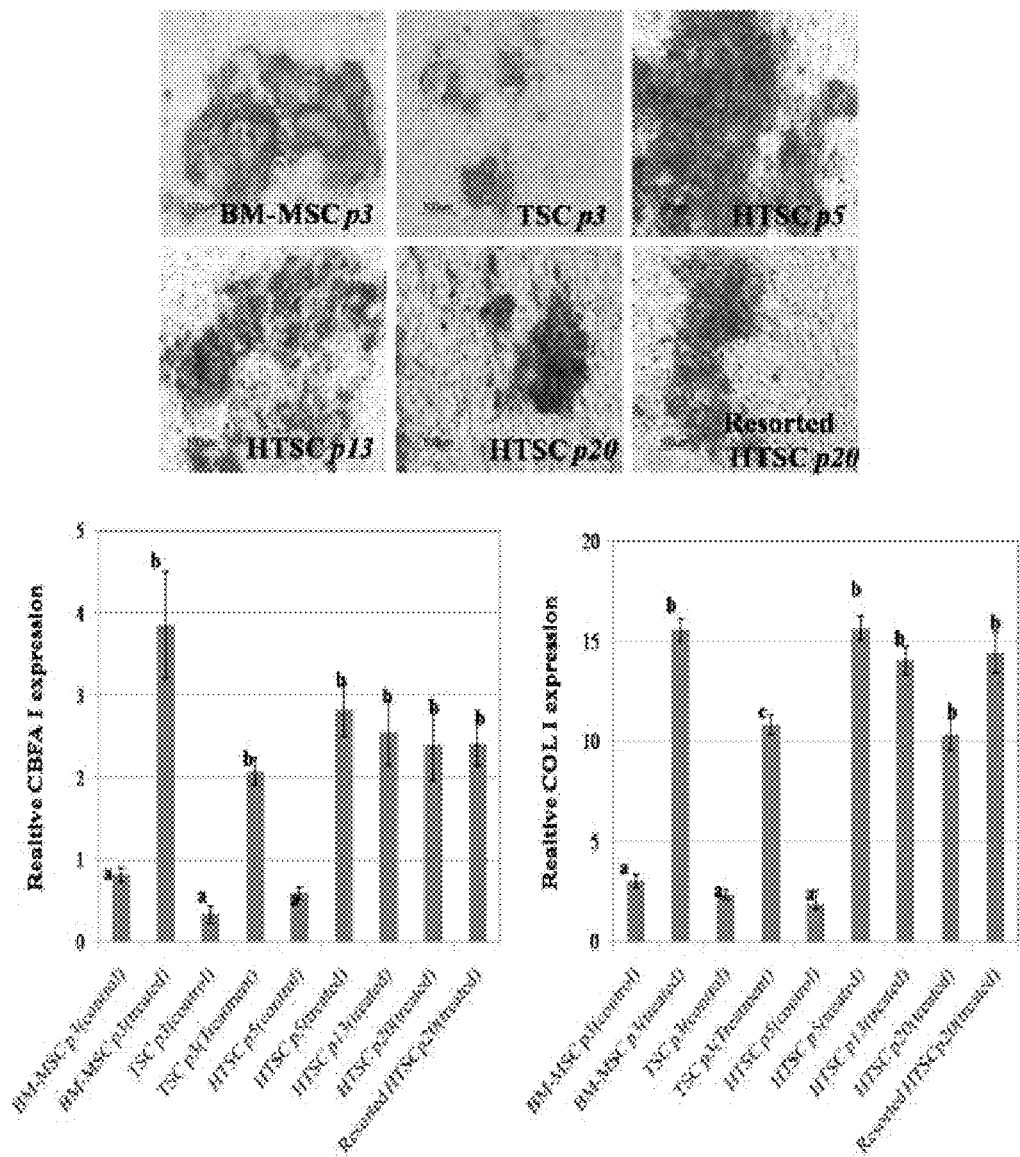
FIG. 5c shows calcium deposits with Alizarin Red S (left panels) and gene expression of CBFA I (the left of right panels) and COL I (the right of right panels) to evaluate osteogenic differentiation.

HTSCs, TSCs and BM-MSCs were also placed in osteogenic medium for 3 weeks. Under this condition, derivatives from all HTSCs and BM-MSCs were positively stained for Alizarin Red S, an indicator of calcium production. And also, both types of cells showed similar expression levels of osteocyte marker genes, COL I and CBFA I (FIG. 5c). However, the intensity of staining and the osteocyte gene expression were low in TSCs.

Figure 14:
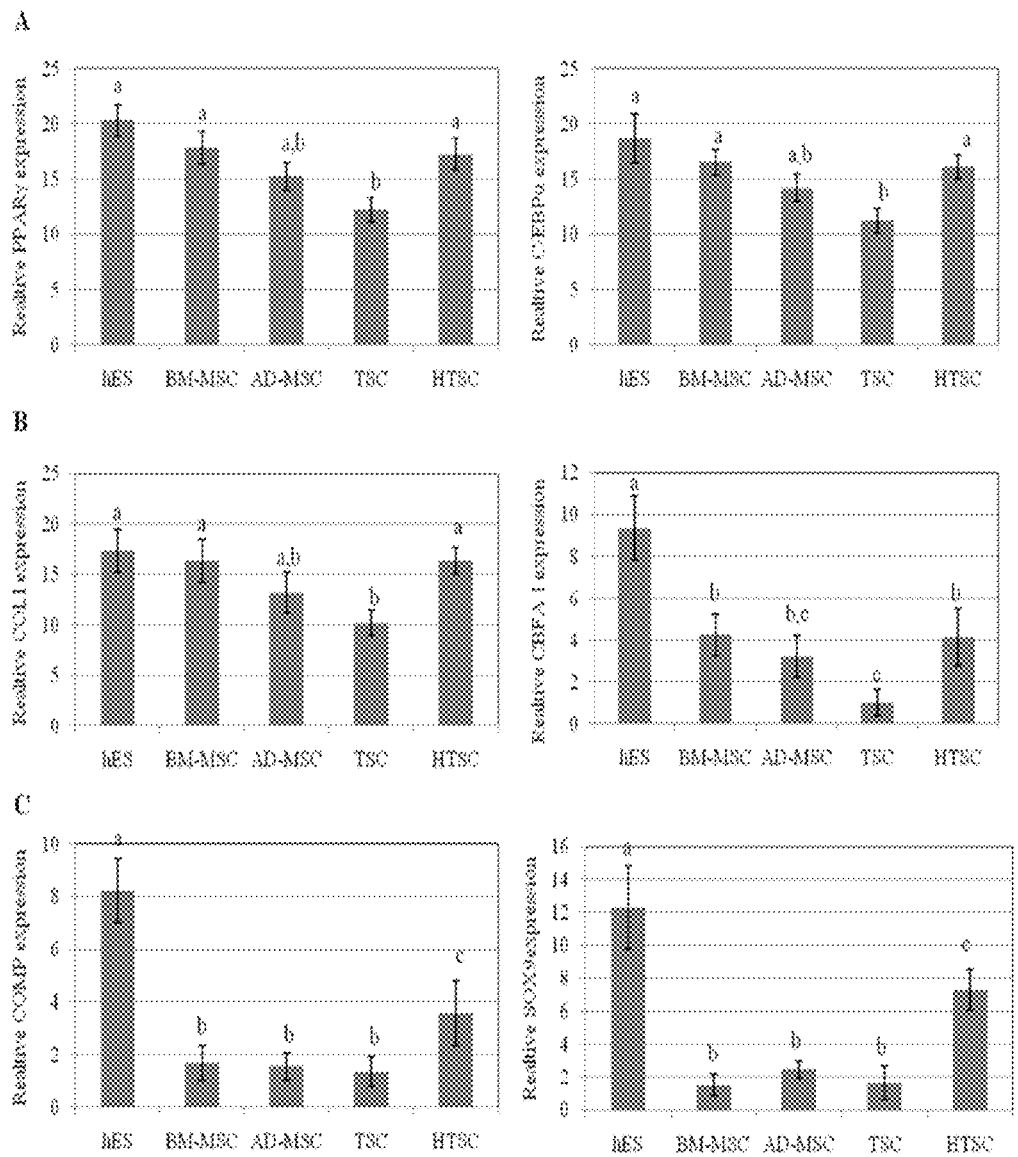
FIG. 14 shows in vitro differentiation potentials into mesodermal-lineage (adipogenic, osteogenic and chondrogenic) cells of embryonic stem cells (ESCs), bone marrow-derived mesenchymal stem cells (BM-MSCs), adipose-derived (AD)-MSCs, testis-derived stem cells (TSCs), and highly proliferative testis-derived stem cells (HTSCs). (A) represents gene expression of PPARγ (upper left) and C/EBPα (upper right). (B) represents Gene expression of COL I (middle left) and CBFA I (middle right). (C) represents gene expression of COMP (lower left) and SOX9 (lower right).

(5) Gene Expression Profiles of Various Stem Cells after Differentiations to Chondrogenic, Adipogenic, and Osteogenic Cells Comparative analyses of differentiation potential among ESCs, BM-MSCs, adipocyte-derived hMSCs (AD-MSC), TSCs, and HTSCs were carried out by examining the relative expression levels of specific genes involved in chondrogenesis, adipogenesis, and osteogenesis (FIG. 14). The chondrogenic potential of HTSCs was significantly higher (p≤0.001) than those of BM-MSCs, AD-MSCs and TSCs, although not as good as that of ESCs. The adipogenic potential of HTSCs was comparable to that of ESCs and BM-MSCs, but superior to those of AD-MSCs and TSCs.

(6) In Vitro Differentiation into Neurogenic Cells

Figure 15B:
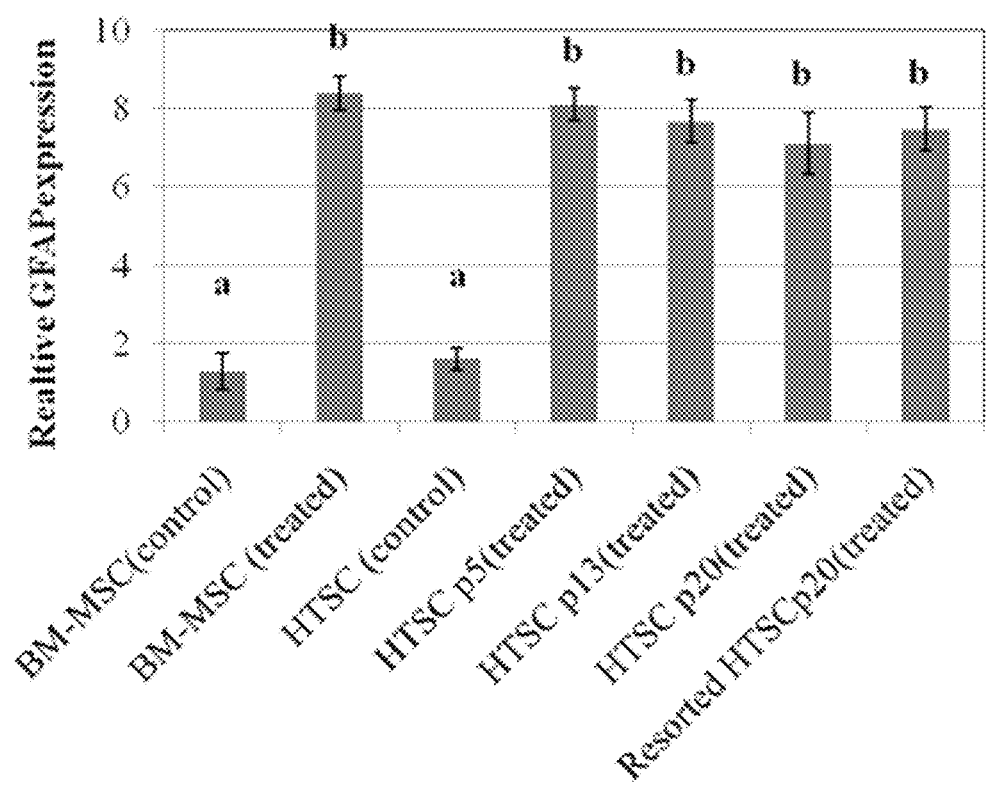
FIG. 15b shows phase contrast photomicrograph of differentiated neuronal cells from BM-MSCs and HTSCs (100×).

HTSCs at p5, 13 and 20, resorted HTSCs at p20, and BM-MSCs at p3 were cultured in neurogenic step I medium for 3 days. At the end of this step, some derivatives from HTSCs and BM-MSCs were positively stained with anti-nestin antibody (FIG. 15a). When these nestin-positive cells were cultured in neurogenic step II medium for another 3 days, the morphology of derivatives from HTSCs and BM-MSCs changed into the bipolar form characteristics of neurons. And also, expression of neural cell-specific genes of GFAP and 6-tubulin 3 was observed in the bipolar cells from both HTSCs and BM-MSCs (Supporting Information FIG. 15b).

(7) In Vitro Differentiation into Insulin-Secreting Cells

Figure 6A:
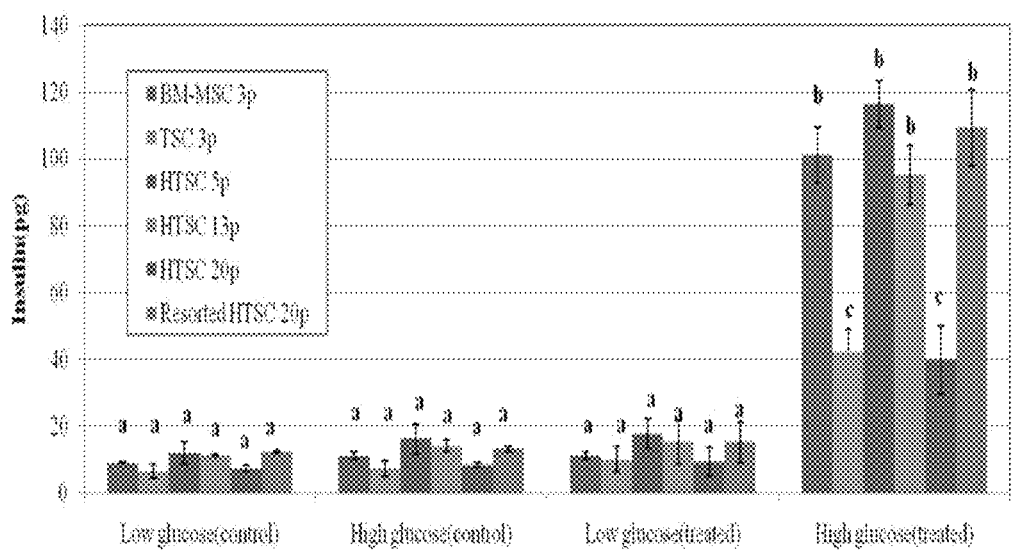
FIG. 6a and FIG. 6b show the results of enzyme-linked immunosorbent assay to measure the secretion of insulin and C-peptide after culture in various differentiation conditions.
Figure 6B:
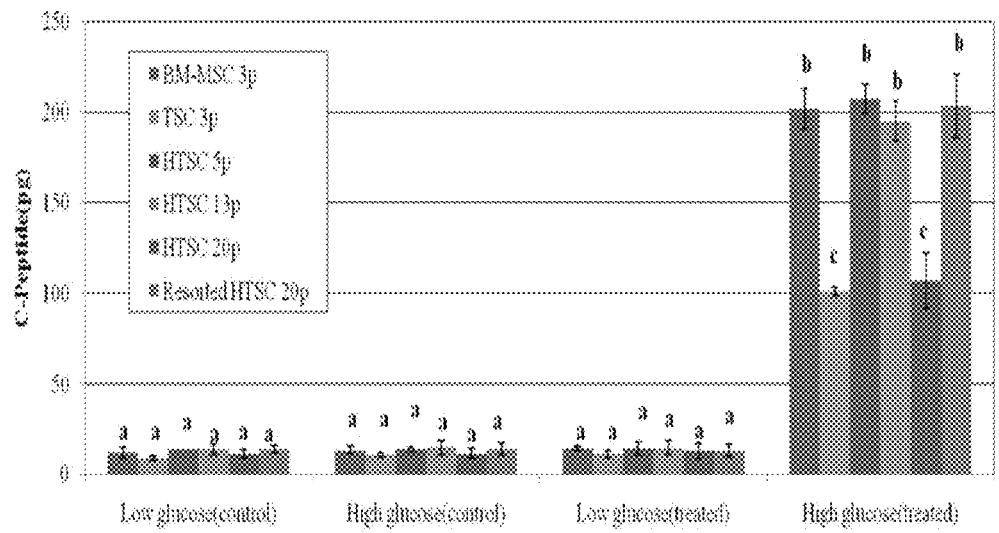
Figure 6C:
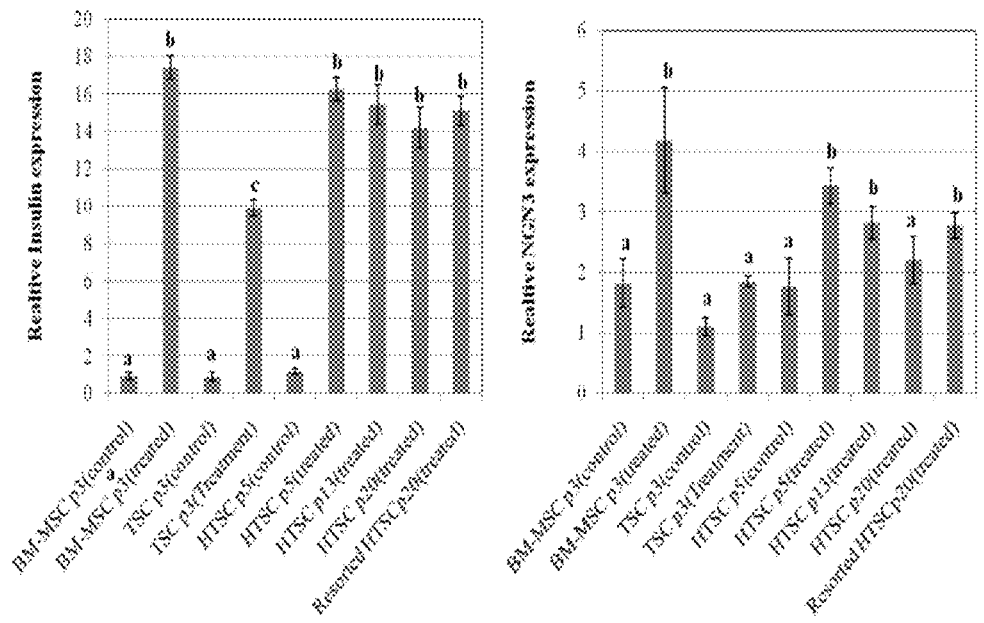
FIG. 6c shows comparison of insulin and NGN-3 gene expression between insulinogenic cells derived from HTSCs and BM-MSCs.

The mesodermal lineage multipotencies of HTSCs, resorted HTSCs, and BM-MSCs were also examined by differentiating them into insulin-secreting cells in vitro. After culture in insulinogenic media, insulin-secreting activity, particularly the glucose-dependent secretion of the cells, was analyzed by stimulating the cells with a low (5.5 mM) or high (25 mM) concentrations of glucose. When the cells were not induced to differentiate, the amounts of insulin and C-peptide released into the medium in response to either glucose stimulation were similar for all HTSCs (at p5, p13, p20, and resorted p20) and BM-MSCs (p3). After culturing the same cells in the differentiation medium, insulin and C-peptide release by the cells were greatly increased by high-glucose stimulation. When stimulated with high glucose, HTSCs at p5 and p13 secreted similar amounts of insulin and C-peptide as BM-MSCs at p3. By p20, HTSCs showed a decline in their capacity to secrete insulin and C-peptide, but resorting for CD34 at p8 rescued this decline and enabled the cells to maintain high insulin and C-peptide secretion at p20 (FIG. 6a and FIG. 6b). And also, the pancreatic beta-cell marker genes of insulin and NGN3 were distinctly expressed in all HTSCs and BM-MSCs that were cultured in insulinogenic differentiation media, but not in undifferentiated cells (FIG. 6c).

(8) In Vivo Differentiation of Adipogenic, Osteogenic, and Chondrogenic Cells

Figure 16A:
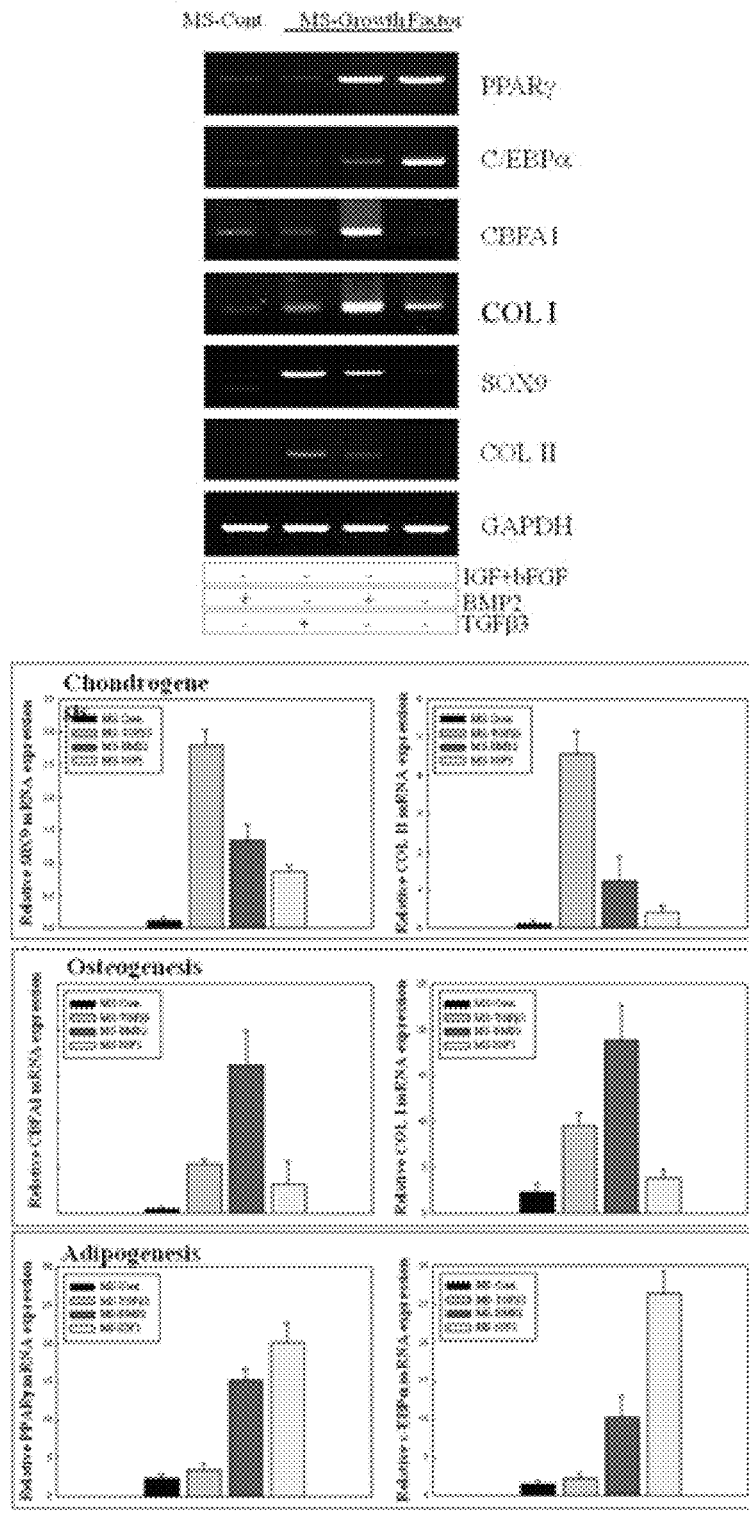
FIG. 16a and FIG. 16b show gene and protein expression of PPARγ and C/EBPα in HTSCs undergoing adipogenic differentiation, COL I and CBFA I in HTSCs undergoing osteogenic differentiation, and COMP and SOX9 in HTSCs undergoing chondrogenic differentiation compared to non-induced HTSCs.

HTSCs loaded in growth factor-containing microspheres were divided into 4 groups and then were transplanted subcutaneously onto the backs of 10 nude BALB/c female mice. The expression of differentiation-associated genes, including PPARγ, C/EBPα, CBFA I, COL I, SOX 9 and COL II, were detected by RT-PCR. Gene characteristics of adipogenic, osteogenic, and chondrogenic cells were highly expressed in differentiating HTSCs transplanted with specific growth factor-containing microspheres (FIG. 16a).

Figure 16B:
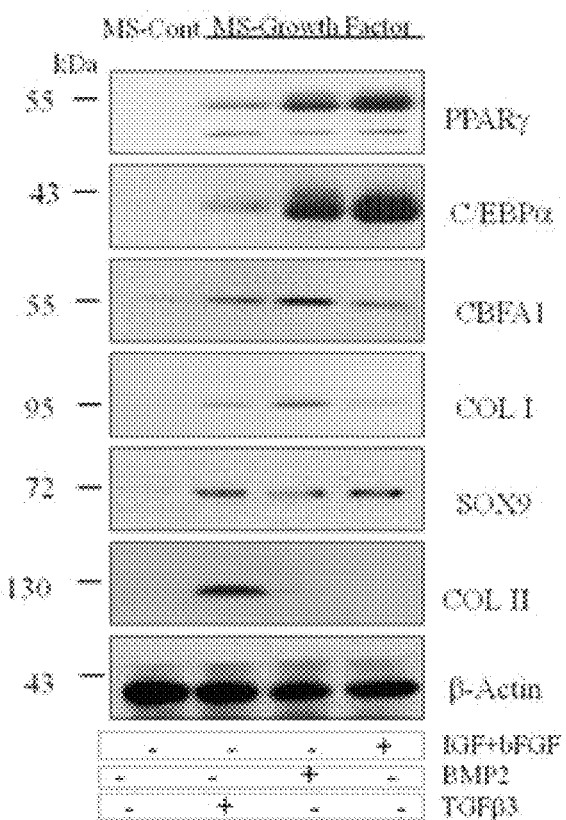
Figure 16C:
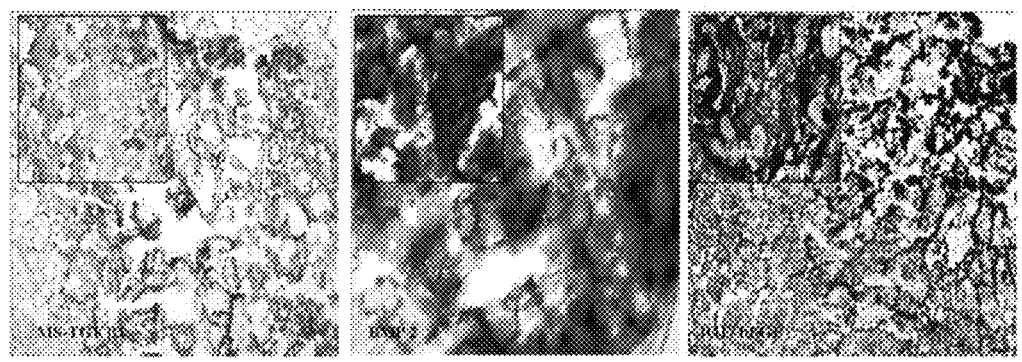

Western blot analyses showed the presence of the corresponding proteins in the sera of these mice (FIG. 16b). Further, specific staining or immunocytochemical analysis using specific markers demonstrated the adipogenic, osteogenic and chondrogenic differentiation potential of HTSCs both in vivo and in vitro (FIG. 16c and FIG. 16d).

Figure 7B:
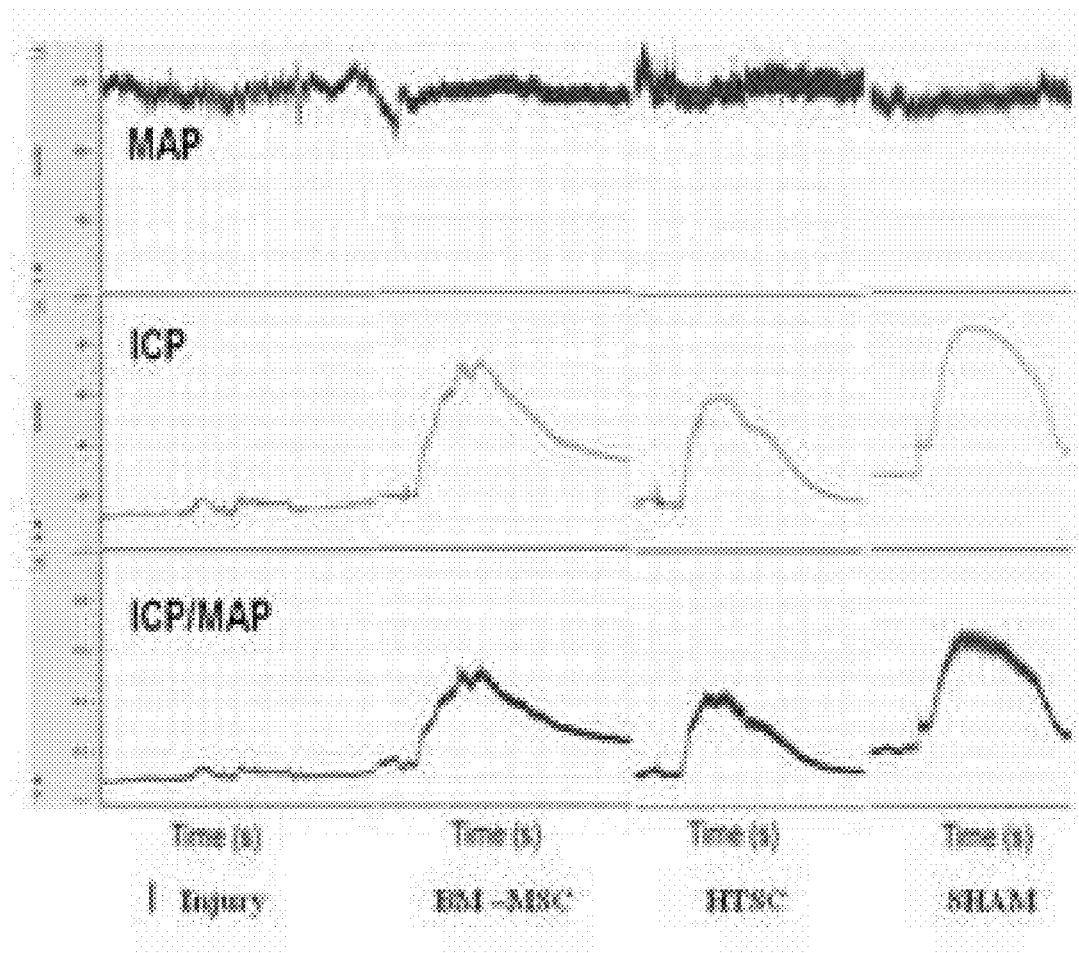
FIG. 7b shows results of the measurement of erectile function, in which the red, blue and green curves represent the mean arterial pressure (MAP), intracavernous pressure (IAP) and ICP/MAP ratio, respectively in response to nerve stimulation.
Figure 7C:
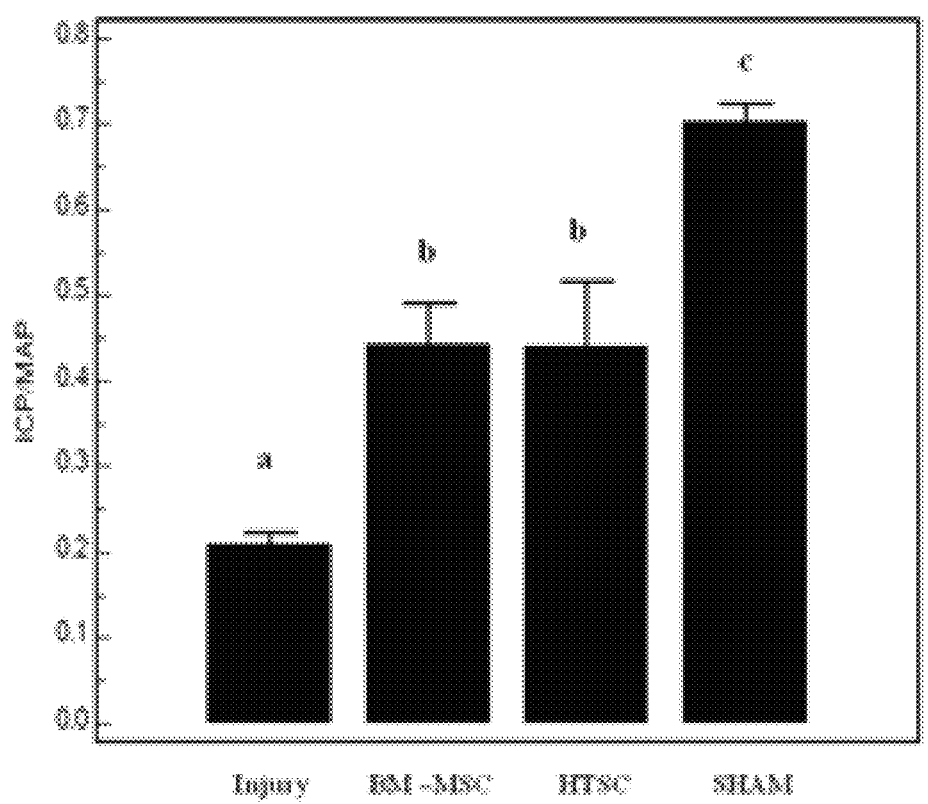
FIG. 7c shows that injection of bone marrow-derived mesenchymal stem cells (BM-MSCs) and human highly proliferative testis-derived stem cells (HTSCs) increased the ICP/MAP ratio compared with injury alone.
Figure 7D:
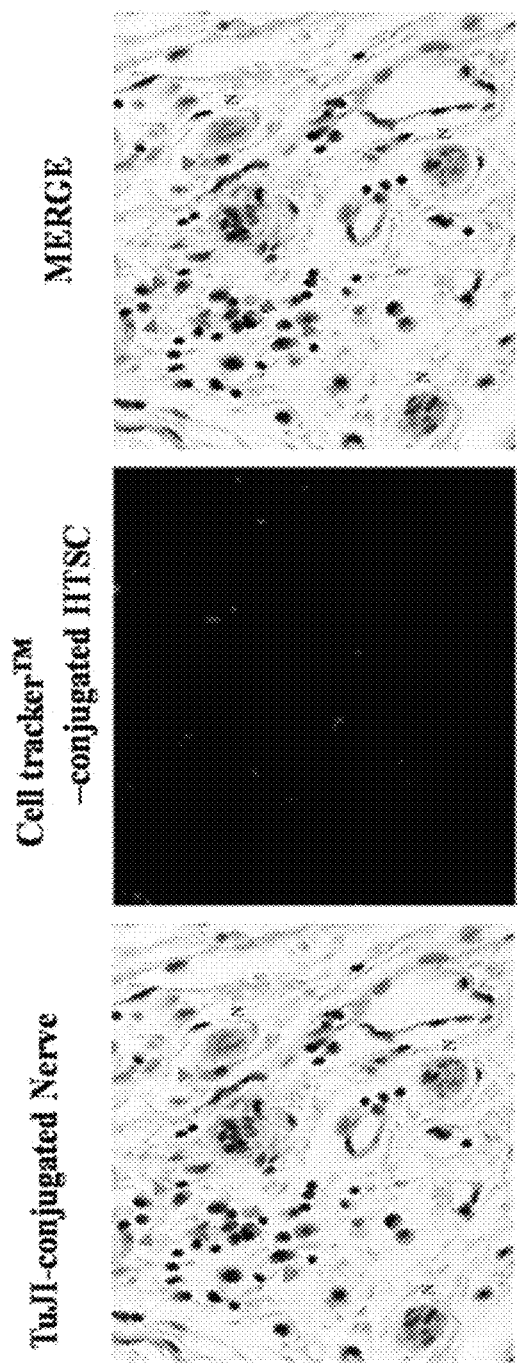
FIG. 7d shows the perineural prostatic tissue stained with CellTracker (red fluorescence) and a neuron marker (TuJI, dark brown) to visualize HTSCs (arrowheads).
Figure 7E:
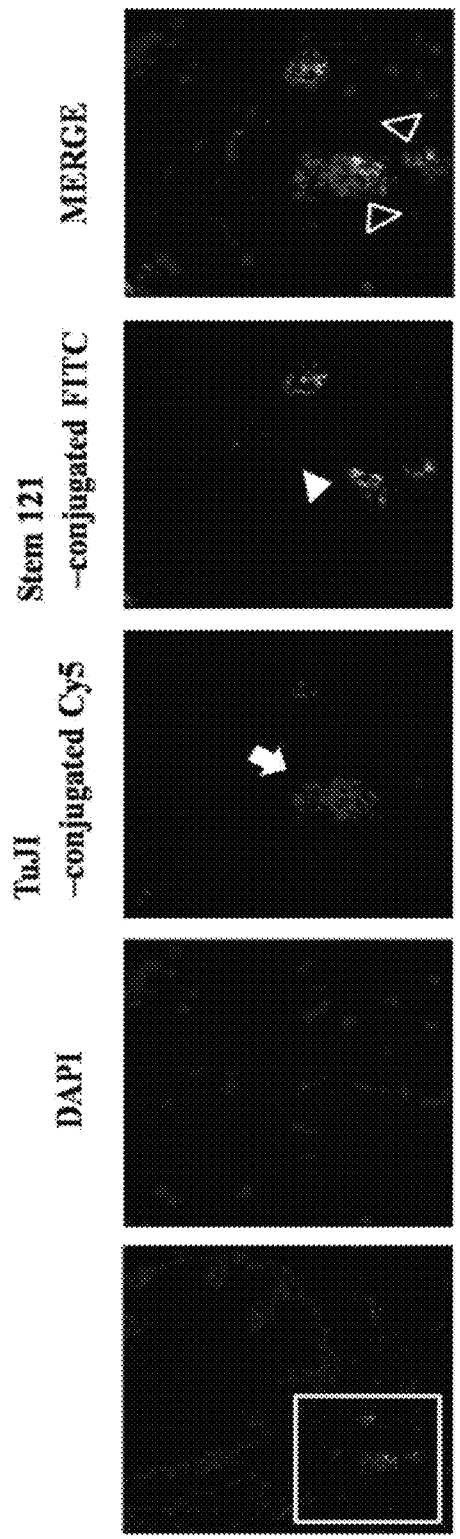
FIG. 7e shows TuJI (pupple, arrow) and human cell-specific antibody Stem 121 (green, white arrowhead). DAPI nuclear staining is in blue; CellTracker is in red (open arrowheads).

(9) Functional Recovery of Bilateral Cavernous Nerve Crush Injury (BCNCI) from Transplanted HTSCs We used a bilateral cavernous nerve crush injury model in rats to examine the possibility of using HTSCs in a clinically relevant cell-based therapy. HTSCs or BM-MSCs were periprostatically injected into rats whose cavernous nerve had been damaged on both sides. Functional recovery of the crush injury area, systemic mean arterial pressure (MAP) and intracavernosal pressure (ICP) were evaluated to compare the therapeutic effects of HTSCs to those of BM-MSCs (FIGS. 7a and 7b). The mean ICP/MAP ratio was significantly lower in the injury group (0.20±0.01) compared to the sham group (0.70±0.02) (p<0.001) (Table 2, FIG. 7c). Periprostatic injection of either BM-MSCs or HTSCs resulted in a significant increase of the ICP/MAP ratio compared with the injury group (p<0.001). Upon stimulation of the distal portion of the cavernous nerve, partial recovery of the erectile response was seen in both the BM-MSC group (0.44±0.05) and the HTSC group (0.44±0.07) without any significant difference between the two groups. In the prostates of treated animals, cells of human origin were detected with CellTracker™ CM-DiI (red color) and were also found to be TuJi(neuron)-positive, indicating that the injected HTSCs had incorporated around the rat cavernous nerve and had differentiated into neuronal cells (FIG. 7d). In addition, we have also found that the Stem-121™ (FITC, green color, arrowhead) and TuJI (Cy5, purple color, arrow)-double-positive cells in the crush injury area and some CellTracker™ CM-DiI (red color, open arrow heads) were observed. Therefore, these results show that injected HTSCs can differentiate and integrated into neurons (FIG. 7e).

TABLE 2

| Groups | Injury | BM-MSC | HTSC | Sham | p value |
|---|---|---|---|---|---|
| MAP (cm-$H_2O$) | 136.6 ± 4.1 | 142 ± 5.8 | 135.2 ± 3.9 | 135.6 ± 3.2 | 0.675 |
| ICP (cm-$H_2O$) | 27.2 ± 3.3 | 60.2 ± 6.3 | 58.6 ± 11.5 | 86.7 ± 2.6 | 0.001 |
| ICP/MAP ratios | 0.20 ± 0.014 | 0.44 ± 0.048 | 0.44 ± 0.073 | 0.70 ± 0.019 | <0.001 |

(10) Correlation Between CD34 Expression and Cell Differentiation

Figure 17A:
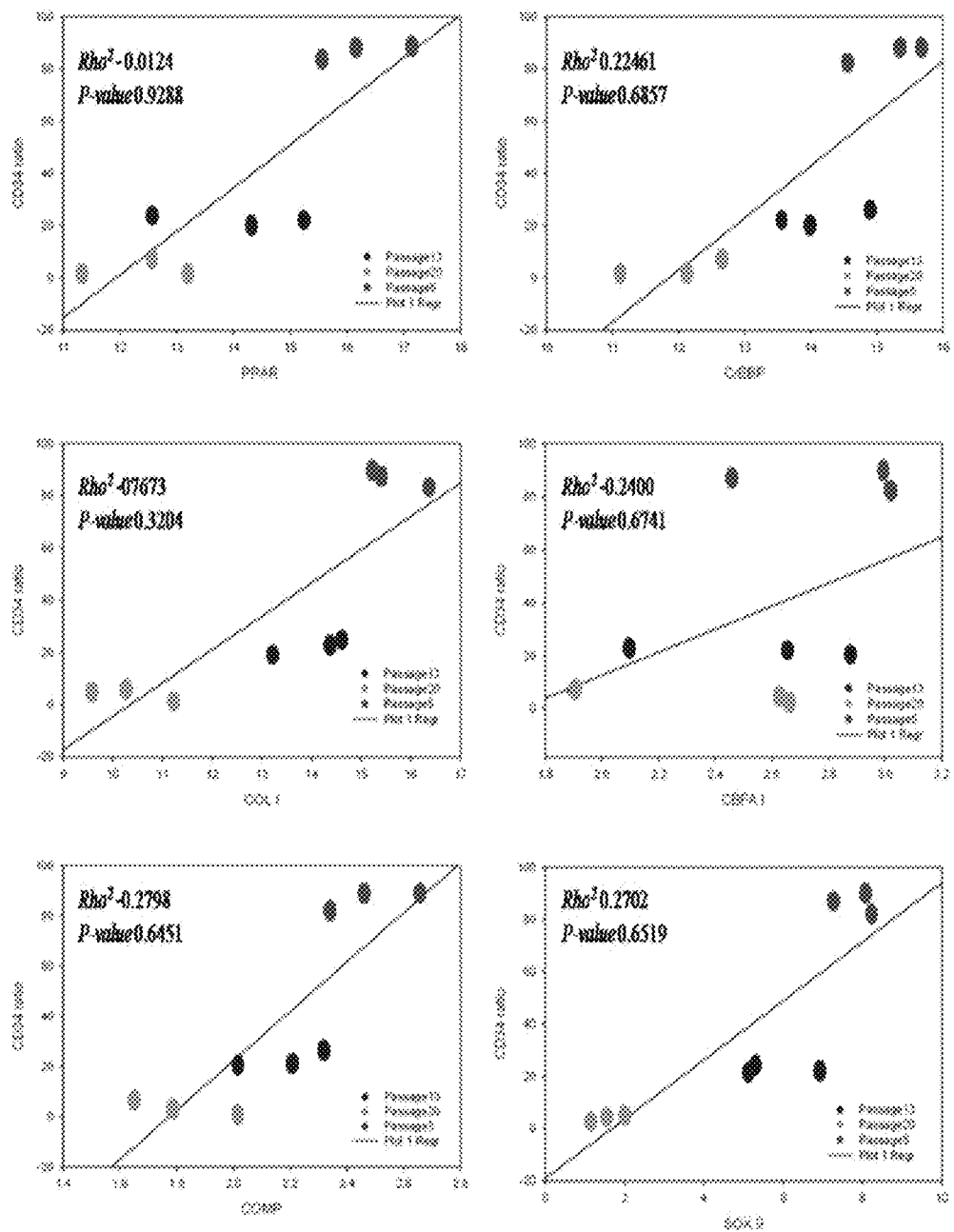
FIG. 17a and FIG. 17b show the results obtained from the analyses for the proportion of cells expressing CD34 and the degree of differentiation of the cells. The proportion of cells expressing CD34 decreased with passaging (passages 5, 13, and 20) and the marker gene expression levels of all three germ layer lineages (mesodermal genes: PPAR, C/EBP, COL I, CBFA I, COMP, and SOX9; endodermal genes: Insulin and NGN; and ectodermal genes: GFAP and 6-Tubulin 3) also decreased.
Figure 17B:
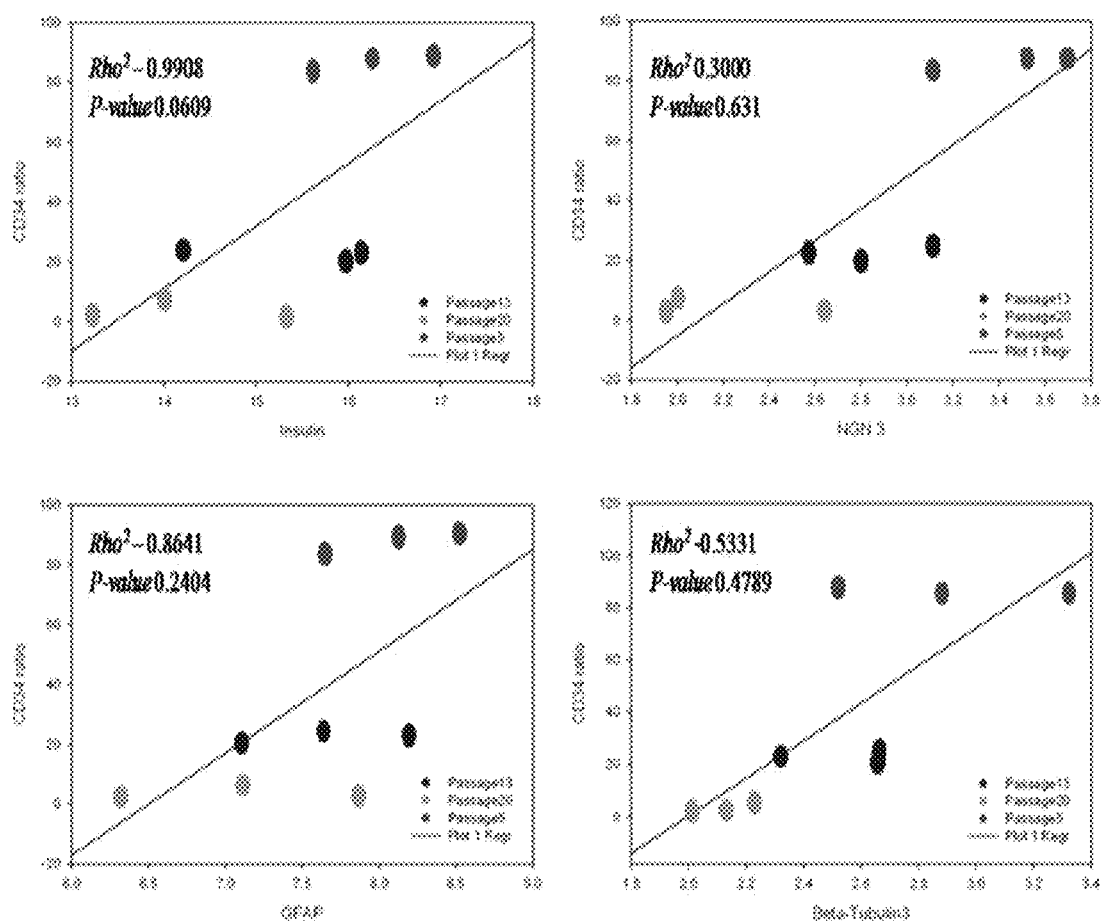

The proportion of cells expressing CD34 and the degree of differentiation of the cells were analyzed. As the proportion of cells expressing CD34 decreased during subsequent passaging (p5, p13, and p20), the gene expression levels of markers of all three germ layer lineage cells also decreased. The expression of mesodermal genes: PPARγ, C/EBPα, COL I, CBFA I, COMP, and SOX9, endodermal genes: Insulin and NGN; and ectodermal genes: GFAP and β-Tubulin 3 was significantly down-regulated (FIG. 17a and FIG. 17b).

3. Discussion

In this study, the present inventors isolated and characterized HTSCs from human testis tissue. Since the report from Kanatsu-Shinohara et al. (2004) regarding testicular mouse multipotent spermatogonial stem cells (SSCs) (Kanatsu-Shinohara M, Inoue K, Lee J, et al. Generation of pluripotent stem cells from neonatal mouse testis. Cell. 2004; 119:1001-1012), many studies have been focused on isolating, characterizing, and propagating their human counterparts (Conrad S, Renninger M, Hennenlotter J, et al. Generation of pluripotent stem cells from adult human testis. Nature. 2008; 456:344-349; Kossack N, Meneses J, Shefi S, et al. Isolation and characterization of pluripotent human spermatogonial stem cell-derived cells. Stem Cells. 2009; 27:138-149; Golestaneh N, Kokkinaki M, Pant D, et al. Pluripotent stem cells derived from adult human testes. Stem Cells Dev. 2009; 18:1115-1126; Mizrak S C, Chikhovskaya J V, Sadri-Ardekani H, et al. Embryonic stem cell-like cells derived from adult human testis. Hum Reprod. 2010; 25:158-167). These isolated human cells are thought to originate from SSCs, though their exact origins are controversial (Conrad S, Renninger M, Hennenlotter J, et al. Generation of pluripotent stem cells from adult human testis. Nature. 2008; 456:344-349; Tapia N, Arauzo-Bravo M J, Ko K, et al. Concise review: challenging the pluripotency of human testis-derived ESC-like cells. Stem Cells. 2011; 29:1165-1169; Chikhovskaya J V, Jonker M J, Meissner A, et al. Human testis-derived embryonic stem cell-like cells are not pluripotent, but possess potential of mesenchymal progenitors. Hum Reprod. 2012; 27:210-221). Collectively, all designated testicular stem cells from previous studies seem to have originated from testicular germ cells, not from somatic cells. These cells have ESC-like colony morphology and have different characteristics from human HTSCs in terms of stem ness gene expression. Although the HTSCs exhibit similar morphology and characteristics to human testicular MSC-like cells and BM-MSCs, the HTSCs are different from other known MSCs or MSC-like cells in that they initially co-express both CD34 and CD73, contrary to the classical definition of MSCs, which have been characterized by the presence of CD73, CD90, and CD105 membrane antigens but the lack of expression of other cell marker genes (CD34 and CD45). Thus, the HTSCs are novel stem/progenitor cells from human testis somatic cells. That is, the CD34/CD73-double-positive cells are very rare in vivo (FIG. 1) and they constituted only 0.03% of the initially CD73-sorted TSC cell population (FIG. 2a). In addition, our finding of the lack of CD31/CD34-double-positive cells in the testis and the lack of any CD73 expression in the basal lamina of the seminiferous tubules (FIG. 1) led us to suggest that CD34/CD73-double-positive cells (HTSCs) existed in interstitial cells and could be mesenchymal or precursor cells for the interstitial cells.

Although considered a hallmark of hematopoietic stem cells, CD34 is actually expressed in a wide variety of non-hematopoietic tissues and cells, such as vascular endothelial cells and soft tissue neoplasms. In human adipose-derived stem cells, CD34 expression is detected but decreases over time in culture, which may be related to their replicative capacity, differentiation potential, and immaturity or stemness of the cells. To isolate stem cells with regenerative potential from human testicular biopsied samples, the present inventors chose CD73 as an additional selection marker to use along with CD34, as CD73 is constitutively expressed in various MSCs.

CD34/CD73-double-positive HTSCs displayed a higher proliferative capacity than CD34-negative/CD73-positive TSCs. An extremely small number of HTSCs were able to proliferate and expand into a remarkably large population after cultivation for more than 23-32 passages. The capability of these cells to proliferate and differentiate was strongly related to their CD34 level. As shown in FIG. 17, CD34 expression was inversely related to the differentiation state of these cells. As the cells differentiated towards a specific cell type, CD34 expression decreased indicating that CD34 is indeed a stemness/juvenility marker of this type of stem cell. Additionally, similar to the adipose-derived stem cells mentioned above, we found that the proportion of HTSCs that were CD34-positive cells and their proliferative potential declined with successive passages. In contrast, the expression of CD73 was not affected by the duration of culture; it showed consistently high expression through more than 30 passages (FIG. 4b). Resorting for CD34 helped extend the proliferative capacity of the culture and improved the differentiation potential as well. Resorting for CD34 eliminates CD 34$^-$/CD73$^+$ cells, leaving only CD34$^+$/CD73$^+$ cells. Because the differentiation of the HTSCs into specific cell types also causes downregulation of CD34, and long-term culture usually causes senescence and differentiation, the extent of CD34 expression on the testis stromal cells could be a useful selection marker for young and healthy stem cells. Furthermore, because of the close relationships between CD34 expression and cell stemness and longevity, it would be of great interest to determine if overexpression or prolonged expression of CD34 on testis stromal cells can increase the lifespan and plasticity of the cells.

The HTSCs possessed common characteristics of MSCs, but not of ESCs (FIG. 2c). The present inventors directly compared the differentiation potential of various types of stem cells: ESCs, BM-MSCs at p3, TSCs at p5 and HTSCs at p5. In in vitro and in vivo differentiation studies, HTSCs were able to differentiate into adipogenic, osteogenic, and chondrogenic cells in a manner comparable to that of BM-MSCs (FIG. 5 and FIG. 14). HTSCs were also able to differentiate into neurogenic cells and insulin-secreting cells when specific protocols were applied (FIG. 15 and FIG. 6).

In the in vivo cell transplantation study, undifferentiated HTSCs supported the recovery from bilateral cavernous nerve crush injury and the recovery of blood flow in an injured rat model after 4 weeks of initial cell injection (FIG. 7). Radical prostatectomy for prostate cancer often results in an erectile dysfunction caused by the damage to the neurovascular bundle (cavernous nerve) that resides along the posterolateral region of the prostate. The present inventors found that periprostatic injection of HTSCs or BM-MSCs around the crush injury area improved erectile function. In fact, we found exogenous HTSC-derived neurons inside of the cavernous nerve of these rat (FIG. 7e) and observed functional improvement of blood pressure. In the present study, after HTSC injection, some neurons (TuJI-positive cells) around the injury site were also positive for a human cell pre-stained marker (CellTracker™ CM-Dil) and a human-specific antibody, indicating that the injected HTSCs have the potential to differentiate into neuronal cells after transplantation (FIG. 7d and FIG. 7e). Thus, if a patient were diagnosed with prostate cancer, our method could be used to obtain, expand and store the autologous stem cells (HTSCs) from testis biopsies for the treatment of erectile dysfunction in the future.

The testes contain not only germ cells but also different types of culture-induced pluripotent stem cells. The culture-induced stem cells can be used for patient-specific cell therapy without significant ethical issues, but the efficiency of establishing stem cell lines is still extremely low, and the cell lines that have been isolated are not well characterized in humans (Ko K, Arauzo-Bravo M J, Tapia N, et al. Human adult germline stem cells in question. Nature. 2010; 465:E1, discussion E3). Moreover, the stem cell lines established using spermatogonial germ cells develop into tumors after injection into NOD-SCID mice (Seandel M, James D, Shmelkov S V, et al. Generation of functional multipotent adult stem cells from GPR125+ germline progenitors. Nature. 2007; 449:346-350), casting doubt on their clinical uses in human medicine. In the present study, the present inventors have established multiple stem cell lines using defined culture conditions and a simple, high efficient MACS system (100% isolation rate) from donors with normal (2 of obstructive azoospermia) and abnormal testis physiology (13 of non-obstructive azoospermia without germ cells). Generally, human adult stem cells can only replicate a limited number of times and enter the senescence phase shortly after isolation and in vitro expansion. In addition, human adult stem cells have a high incidence of chromosomal abnormalities during in vitro expansion. In the present study, none of the cell lines tested developed tumors in immunodeficient mice, and chromosomal integrity was maintained up to passage 30, indicating that these cell lines are safe alternatives to human embryonic stem cells. Moreover, because there was no difference between isolated HTSCs from these two types of male donors with regard to differentiation efficiency, the methods we described could be applicable to all male.

4. Conclusions

The present inventors found that CD34/CD73 co-expression in human testis stromal cells was positively correlated with proliferative capacity, differentiation potential, and juvenescence or stemness. Thus, the CD34 and CD73 can be used as initial selection markers to obtain highly proliferative adult stem cells from a simple testis biopsy. Utilization of these cells may permit patient-specific cell-based therapies without concern for tumor development or ethical controversy, which are issues plaguing the use of human ESCs. Additionally, because of their high proliferation capacity, these CD34/CD73-co-expressing HTSCs seem to be especially useful for therapies requiring a large number of cells.

The invention claimed is:

1. A process of preparing human multipotent stem cells co-expressing CD34 and CD73, comprising: . . .
   (a) isolating outer surrounding cells of seminiferous tubules from a human testis;
   (b) culturing the cells isolated in step (a);
   (c) sorting and isolating cells co-expressing CD34 and CD73 from the cells cultured in step (b) using anti-CD34 and anti-CD73 antibodies;
   (d) culturing the cells isolated in step (c) up to passage 9 in a medium comprising feeder cells and serum;
   (e) . . . such that multipotent stem cells co-expressing CD34 and CD73 are obtained; and
   (f) culturing the multipotent stem cells co-expressing CD34 and CD73 obtained in step (e).

2. The process according to claim 1, wherein the outer surrounding cells of seminiferous tubules are isolated from the human testis using collagenase, dispase, or a mixture thereof.

3. The process according to claim 1, wherein the cells isolated in step (a) are cultured up to passage 4 in culturing of step (b) in a medium comprising feeder cells and serum.

4. The process according to claim 1, wherein the cell-sorting in step (c) and/or step (e) is carried out by magnetic activating-cell sorting.

5. The process according to claim 1, wherein the cells isolated in step (c) is cultured up to passage 7 in step (d) in a medium comprising feeder cells and serum.

6. The process according to claim 1, wherein, the cells isolated in step (e) are cultured up to passage 12 in step (f) in a medium comprising feeder cells and serum.

7. The process according to claim 6, further comprising and isolating the cells cultured in step (f) using an anti-CD34 antibody such that cells co-expressing CD34 and CD73 are obtained, and culturing the isolated cells.

* * * * *

UNITED STATES PATENT AND TRADEMARK OFFICE
CERTIFICATE OF CORRECTION

PATENT NO. : 9,688,961 B2
APPLICATION NO. : 14/126220
DATED : June 27, 2017
INVENTOR(S) : Dong-Ryul Lee, Won-Yun Choi and Tae-Ki Yoon It is certified that error appears in the above-identified patent and that said Letters Patent is hereby corrected as shown below:

Column 31, Claim 1, Lines 45-46:
Please delete "comprising: . . . (a)" and replace with -- comprising: (a) --

Column 31, Claim 1, Line 54:
Please delete "(e) . . . such" and replace with -- (e) sorting and isolating the cells cultured in step (d) using an anti-CD34 antibody, such --

Column 32, Claim 5, Lines 50-51:
Please delete "(c) is cultured up to passage 7 in step (d) in a medium comprising feeder cells and serum." and replace with -- (c) are cultured up to passage 7 in step (d). --

Column 32, Claim 6, Lines 52-53:
Please delete "wherein, the cells isolated in step (e)" and replace with -- wherein the multipotent stem cells co-expressing CD34 and CD73 obtained in step (e) --

Column 32, Claim 7, Lines 55-58:
Please delete "claim 6, further comprising and isolating the cells cultured in step (f) using an anti-CD34 antibody such that cells co-expressing CD34 and CD73 are obtained, and culturing the isolated cells." and replace with -- claim 1, further comprising: (g) sorting and isolating the cells cultured in step (f) using an anti-CD34 antibody such that cells co-expressing CD34 and CD73 are obtained; and (h) culturing the multipotent cells co-expressing CD34 and CD73 obtained in step (g). --

Signed and Sealed this
Seventh Day of August, 2018

Andrei Iancu
*Director of the United States Patent and Trademark Office*

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tgaagtgtga cgtggacatc                                              20

<210> SEQ ID NO 2
<211> LENGTH: 20
<212> TYPE: DNA
<213> ORGANISM: Artificial Sequence
<220> FEATURE:
<223> OTHER INFORMATION: primer
```

<400> SEQUENCE: 2
ggaggagcaa tgatcttgat                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agcgaaccag tatcgagaac                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttacagaacc acactcggac                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tgaacctcag ctacaaacag                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tggtggtagg aagagtaaag                                               20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
agctacagca tgatgcagga                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ggtcatggag ttgtactgca                                               20

<210> SEQ ID NO 9
<211> LENGTH: 26

<212> TYPE: DNA
<213> ORGANISM: Artificial Sequence
<220> FEATURE:
<223> OTHER INFORMATION: primer

<400> SEQUENCE: 9
agaaagtagt gatactcaag gaccaa                                        26

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
tgacagagat tagcttcttc aaaagt                                        26

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
agaacatcac ctaccactgc                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
atgtccaaag gtgcaataat                                               20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ccgcacgaca accgcaccat                                               20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
cgctccggcc cacaaatctc                                               20

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
tgtctcataa tgccatcagg ttg                                           23

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
gataacgatg gtgatttgtc tgtt                                          24

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gcaaactcac cgctccaaat g                                             21

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
ttaggttcca agccatcagg tttg                                          24

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
aacgctgaaa gatcacgctc ac                                            22

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
ggtaccaaag atgaagccc                                                19

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
ttcatgaaga gaccgacga                                                19

<210> SEQ ID NO 22
<211> LENGTH: 20
<212> TYPE: DNA
<213> ORGANISM: Artificial Sequence

```
<220> FEATURE:
<223> OTHER INFORMATION: primer

<400> SEQUENCE: 22
cacaccatga aggcgttcat                                                   20

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
ctggaggttg agagggacaa tct                                               23

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
tactgcgtgc ggatctcttt c                                                 21

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gccaagttct gggaagtcat                                                   20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ggcctgaaga gatgtccaaa                                                   20

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
cgtgaactcc ttgaactgag cag                                               23

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
tggcactcct gggacaaatt tc                                                22
```

```
<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
aaccaacacc tgtgcggctc                                                     20

<210> SEQ ID NO 30
<211> LENGTH: 24
<212> TYPE: DNA
<213> ORGANISM: Artificial Sequence
<220> FEATURE:
<223> OTHER INFORMATION: primer

<400> SEQUENCE: 30
aagggcttta ttccatctct ctcg                                                24

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
cgctgagtac gtcgtggagt                                                     20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
atgatgttct ggagagcccc                                                     20
```